(12) United States Patent
Boyer et al.

(10) Patent No.: US 11,999,757 B2
(45) Date of Patent: Jun. 4, 2024

(54) SYNTHESIS OF BORONATE ESTER DERIVATIVES AND USES THEREOF

(71) Applicant: MELINTA SUBSIDIARY CORP., Parsippany, NJ (US)

(72) Inventors: Serge Henri Boyer, San Diego, CA (US); Scott J. Hecker, Del Mar, CA (US); Gerardus K. M. Verzijl, Well (NL); Petrus J. Hermsen, Horst (NL)

(73) Assignee: MELINTA SUBSIDIARY CORP., Parsippany, NJ (US)

( * ) Notice: Subject to any disclaimer, the term of this patent is extended or adjusted under 35 U.S.C. 154(b) by 0 days.

(21) Appl. No.: 16/760,369

(22) PCT Filed: Oct. 30, 2018

(86) PCT No.: PCT/US2018/058143
§ 371 (c)(1),
(2) Date: Apr. 29, 2020

(87) PCT Pub. No.: WO2019/089542
PCT Pub. Date: May 9, 2019

(65) Prior Publication Data
US 2020/0308197 A1    Oct. 1, 2020

Related U.S. Application Data

(60) Provisional application No. 62/580,343, filed on Nov. 1, 2017.

(51) Int. Cl.
| | | |
|---|---|---|
| C07F 5/02 | (2006.01) | |
| B01J 23/46 | (2006.01) | |
| C07C 67/31 | (2006.01) | |
| C07C 69/675 | (2006.01) | |
| C07F 5/04 | (2006.01) | |
| C12P 9/00 | (2006.01) | |

(52) U.S. Cl.
CPC ............ *C07F 5/025* (2013.01); *B01J 23/462* (2013.01); *C07C 67/31* (2013.01); *C07C 69/675* (2013.01); *C07F 5/04* (2013.01); *C12P 9/00* (2013.01)

(58) Field of Classification Search
CPC ....... C07C 69/675; C07C 67/31; C07F 5/025; C07F 5/04; C07F 5/02; B01J 23/462; C12P 41/002; C12P 9/00
See application file for complete search history.

(56) References Cited

U.S. PATENT DOCUMENTS

| | | | |
|---|---|---|---|
| 5,814,622 A | 9/1998 | de Nanteuil et al. | |
| 6,420,597 B2 | 7/2002 | Vollmuller et al. | |
| 6,576,789 B1 | 6/2003 | Haber et al. | |
| 7,641,879 B2 | 1/2010 | Spielvogel et al. | |
| 2003/0171544 A1* | 9/2003 | Riermeier ................. | C12P 7/04 |
| | | | 530/350 |
| 2004/0265978 A1* | 12/2004 | Gupta ..................... | C12N 1/205 |
| | | | 435/155 |
| 2005/0250951 A1* | 11/2005 | Peschko .............. | C07F 15/0053 |
| | | | 549/218 |
| 2014/0051869 A1 | 2/2014 | Mccormack et al. | |
| 2015/0105562 A1 | 4/2015 | Murakami et al. | |
| 2016/0237026 A1 | 8/2016 | Battistini et al. | |

FOREIGN PATENT DOCUMENTS

| | | | | |
|---|---|---|---|---|
| CN | 102965403 A | 3/2013 | | |
| EP | 0774452 A1 | 5/1997 | | |
| EP | 1104750 A1 | 6/2001 | | |
| EP | 1386901 | * | 2/2004 | |
| WO | WO-9723641 A1 | 7/1997 | | |
| WO | WO-2007034909 A1 | * | 3/2007 | ............ C07B 53/00 |
| WO | WO-2012/021455 A1 | 2/2012 | | |
| WO | WO-2013/056163 A1 | 4/2013 | | |
| WO | WO-2013/122888 A2 | 8/2013 | | |
| WO | WO-2014/089365 A1 | 6/2014 | | |
| WO | WO-2015/171430 A1 | 11/2015 | | |
| WO | WO-2019/089542 A1 | 5/2019 | | |

OTHER PUBLICATIONS

Gopalan et al. (Bakers' Yeast Reduction of Alkyl 6-chloro-3-oxohexanoates: Synthesis of ®-(+)-alpha-Lipoic acid, J.Chem. Soc. Perkin Trans. 1, pp. 1897-1900, Published 1990. As cited in the IDS filed Aug. 24, 2020) (Year: 1990).*
WO2007034909 translation (Year: 2007).*
Kometani et al. (NADPH-dependent Reduction of Ethyl Acetoacetate Coupled with Ethanol Oxidation in Kloeckera magna, Biosci. Biotech. Biochem., 61 (8), pp. 1370-1372, Published 1997) (Year: 1997).*
Gopalan et al. (Bakers' Yeast Reduction of Alkyl 6-Chloro-3-oxohexanoates: Synthesis of (R)-(+)-alpha-Lipoic Acid, J. Chem. Soc. Perkin. Trans. I pp. 1897-1900, Published 1990). (Year: 1990).*
Karame, I., et al., "Highly Enantioselective Hydrogenation of β-Alkyl and β-(ϖ-Chloroalkyl) Substituted β-Keto Esters," Synthetic Communications, vol. 37, pp. 1067-1076 with cover p. 11 total pages (2007).
Gopalan, Aravamudan S et al., "Bakers' Yeast Reduction of Alkyl 6-Chloro-3-oxohexanoates: Synthesis of (R)-(+)-α-Lipoic Acid," J. Chem Soc. Perkin Trans. 1 pp. 1897-1900 (1990).

(Continued)

*Primary Examiner* — Yevgeny Valenrod
*Assistant Examiner* — Blaine G Doletski
(74) *Attorney, Agent, or Firm* — Wilmer Cutler Pickering Hale and Dorr LLP

(57) ABSTRACT

Disclosed herein are methods for the preparation of boronate derivatives in the synthesis of antimicrobial compounds and uses thereof. Disclosed herein includes method of making a compound of Formula (B) by reducing the ketone group of the keto-ester compound of Formula (A), and the reduction can be performed using a Ruthenium based catalyst system or using an alcohol dehydrogenase bioreduction system.

16 Claims, 5 Drawing Sheets

(56) References Cited

OTHER PUBLICATIONS

Noyori, R. et al., "Asymmetric Hydrogenation of β-Keto Carboxylic Esters. A Practical, Purely Chemical Access to β-Hydroxy Esters in High Enantiomeric Purity," J. Am. Chem. Soc., vol. 109, No. 19, pp. 5856-5858 (1987).

International Search Report and Written Opinion dated Dec. 19, 2018 by Australian Patent Office as International Searching Authority in International Patent Application No. PCT/US2018/058143 (11 total pages).

Examination Report dated Mar. 25, 2022 by Singaporean Patent Office in Singaporean Patent Application No. 11202003762V (4 total pages).

Communication pursuant to Article 94(3) EPC dated May 25, 2022 by European Patent Office in European Patent Application No. 18874877.6 (4 total pages).

Office Action issued by Republic of Colombia Superintendence of Industry and Trade (Colombian Patent Office) in Colombian Patent Application No. NC2020/0006299 with English translation (18 total pages) dated Jun. 29, 2022.

Beaulieu, P.L., et al., "Practical Synthesis of BILA 2157 BS, a Potent and Orally Active Renin Inhibitor: Use of an Enzyme-Catalyzed Hydrolysis for the Preparation of Homochiral Succinic Acid Derivatives," J. Org. Chem., vol. 64, No. 18, pp. 6622-6634 (received Feb. 19, 1999).

Office Action dated Jul. 25, 2022 by Ministry of Law and Human Rights of the Republic of Indonesia—Directorate General of Intellectual Property (Indonesian Patent Office) in Indonesian Patent Application No. P00202003809 with English translation (6 total pages).

Notification of the Substantive Examination dated Aug. 3, 2022 by Saudi Authority for Intellectual Property (Saudi Arabian Patent Office) in Saudi Arabian Patent Application No. 520411905 with English translation (7 total pages).

Preliminary Office Action dated Sep. 2, 2022 by Brazilian Patent Office in Brazilian Patent Application No. BR112020008498-0 with informal English translation (5 total pages).

Notice of Reasons for Rejection dated Oct. 24, 2022 by Japanese Patent Office in Japanese Patent Application No. 2020-543266 with English translation (8 total pages).

Office Action dated Oct. 25, 2022 by Mexican Institute of Industrial Property (IMPI) in Mexican Patent Application No. MX/a/2020/004425 with English summary (6 total pages).

Office Action dated Dec. 5, 2022 by China National Intellectual Property Administration (CNIPA) in Chinese Patent Application No. 201880079247.3 with English translation (9 total pages).

Office Action dated Feb. 15, 2023 by Mexican Institute of Industrial Property (IMPI) in Feb. 2023 Mexican Patent Application No. MX/a/2020/004425 with English translation (9 total pages).

Notice of Hearing issued Sep. 15, 2023 by office of Intellectual Property India in Indian Patent Application No. 202037020993 (2 total pages).

Examination Report dated Sep. 18, 2023 by Saudi Authority for Intellectual Property in Saudi Patent Application No. 522441593 with English translation (14 total pages).

Notice of Preliminary Rejection dated Oct. 12, 2023 by Korean Intellectual Property Office in Korean Patent Application No. 10-2020-7015638 with English translation (15 total pages).

Examination Report dated Nov. 30, 2023 by Australian Intellectual Property Office in Australian Patent Application No. 2018360502 (2 total pages).

Notification on the Result of Substantive Examination dated Jun. 30, 2023 by Intellectual Property Office of Vietnam in Vietnamese Patent Application No. 1-2020-02894 with English translation (4 total pages).

Examination Report dated Jul. 3, 2023 by Chilean Patent Office in Chilean Patent Application No. 202201109 with English translation (18 total pages).

Notice of Reasons for Rejection dated Jul. 24, 2023 by Japanese Patent Office in Japanese Patent Application No. 2020-543266 (4 total pages).

Examination Report dated Aug. 24, 2023 by European Patent Office in European Patent Application No. 18874877.6 (4 total pages).

Office Action dated Aug. 31, 2023 by China National Intellectual Property Administration in Chinese Patent Application No. 201880079247.3 with English translation (6 total pages) 4 pages.

Ema, T., et al., "Highly Enantioselective Reduction of Carbonyl Compounds Using a Reductase Purified from Bakers Yeast," The Journal of Organic Chemistry, vol. 63, No. 15, pp. 4996-5000 (received Jan. 29, 1998).

Khor, G. K., and Uzir, M. H., "*Saccharomyces cerevisiae*: a potential stereospecific reduction tool for biotransformation of mono- and sesquiterpenoids," Yeast, vol. 28, pp. 93-107 (published online Oct. 11, 2010).

Everaere, K., et al., "Ruthenium(II)-Catalyzed Asymmetric Transfer Hydrogenation of Carbonyl Compounds with 2-Propanol and Ephedrine-Type Ligands," Advanced Synthesis & Catalysis, vol. 345, No. 1+2, pp. 67-77 (accepted Sep. 25, 2002).

Nixon, T. D., et al., "Ruthenium-catalysed transfer hydrogenation reactions with dimethylamine borane," Tetrahedron Letters, vol. 52, pp. 6652-6654 (Available online Oct. 15, 2011).

Menashe, N., et al., "Efficient catalytic Reduction of ketones with formic acid and ruthenium complexes," Journal of Organometallic Chemistry, vol. 514, pp. 97-102 (Received Aug. 4, 1995).

Office Action dated Mar. 27, 2023 by Colombian Patent Office in Colombian Patent Application No. NC2020/0006299 with English translation (22 total pages).

Office Action dated Mar. 27, 2023 by Saudi Authority for Intellectual Property in Saudi Patent Application No. 520411905 with English translation (11 total pages).

Office Action dated Mar. 29, 2023 by Thai Patent Office in Thai Patent Application No. 2001002464 with English translation (6 total pages).

Mansoori, Y., et al., "Esterification of carboxylic acids by tributyl borate under solvent- and catalyst-free conditions," Green Chemistry, vol. 7, pp. 870-873 (First published as an Advance Article on the web Oct. 7, 2005).

Pabon, H. J. J., "A synthesis of curcumin and related compounds," Recueil, vol. 83, pp. 379-386 (Received Dec. 3, 1963).

Van Veen, R., and Bickelhaupt, F., "Synthesis of the 9-mesityl-10-phenyl-9- boraanthracene anion," Journal of Organometallic Chemistry, vol. 43, pp. 241-248 (Received Apr. 10, 1972).

Matteson, D. S., ".alpha.-Halo boronic esters: intermediates for stereodirected synthesis," Chemical Reviews, vol. 89, pp. 1535-1551 (Received Jan. 18, 1989).

Coutts, I. G. C., et al., "Organoboron compounds. Part VIII. Aliphatic and aromatic diboronic acids," Journal of the Chemical Society C: Organic, pp. 488-493 (1970).

Shan, Z., et al., "Selective 1,3-cycloboronation of enantiopure 1,1,4,4-tetrasubstituted butanetetraols: versatile preparation, structural characterization, and properties of chiral cyclic boron-containing bifunctional Lewis acids," Tetrahedron: Asymmetry, vol. 20, pp. 1445-1450 (Available online Jun. 27, 2009).

Tyrrell, E., and Brookes, P., "The Synthesis and Applications of Heterocyclic Boronic Acids," Synthesis, No. 4, pp. 469-483 (Received Oct. 22, 2002).

No Author, "Tributyl borate," last retrieved on Jun. 26, 2023 from https://pubchem.ncbi.nlm.nih.gov/compound/Tributyl-borate (59 total pages).

Office Action dated Apr. 20, 2023 by Colombian Patent Office in Colombian Patent Application No. NC2023/0002965 with English translation (20 total pages).

Office Action dated Apr. 24, 2023 by Australian Patent Office in Australian Patent Application No. 2018360502 (3 total pages).

Office Action issued Dec. 11, 2023 by United Arab Emirates Patent Office in United Arab Emirates Patent Application No. P6000635-2020 (10 total pages).

\* cited by examiner

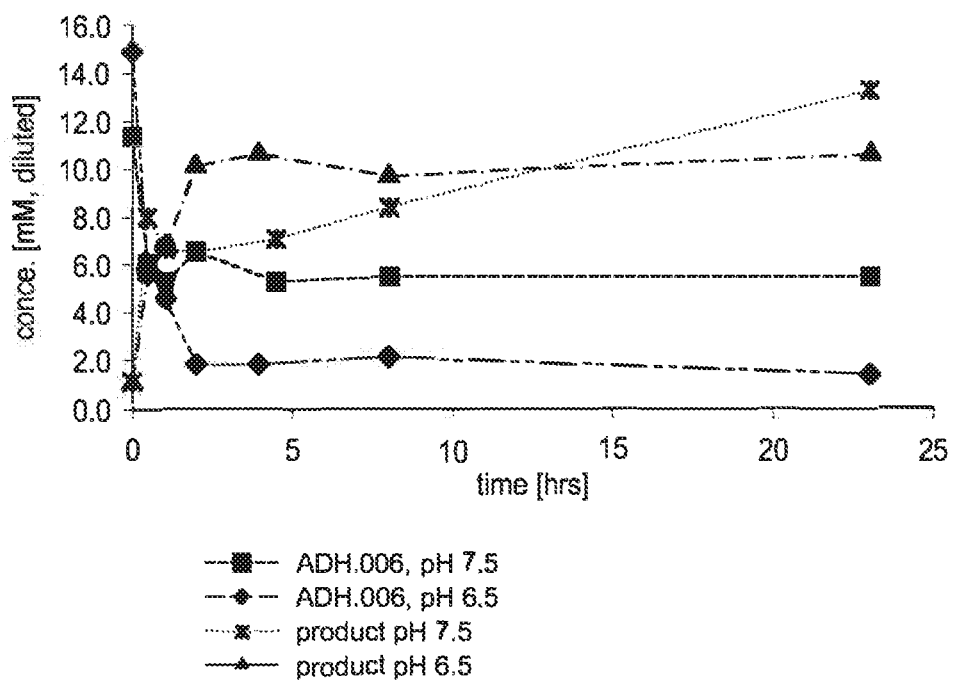

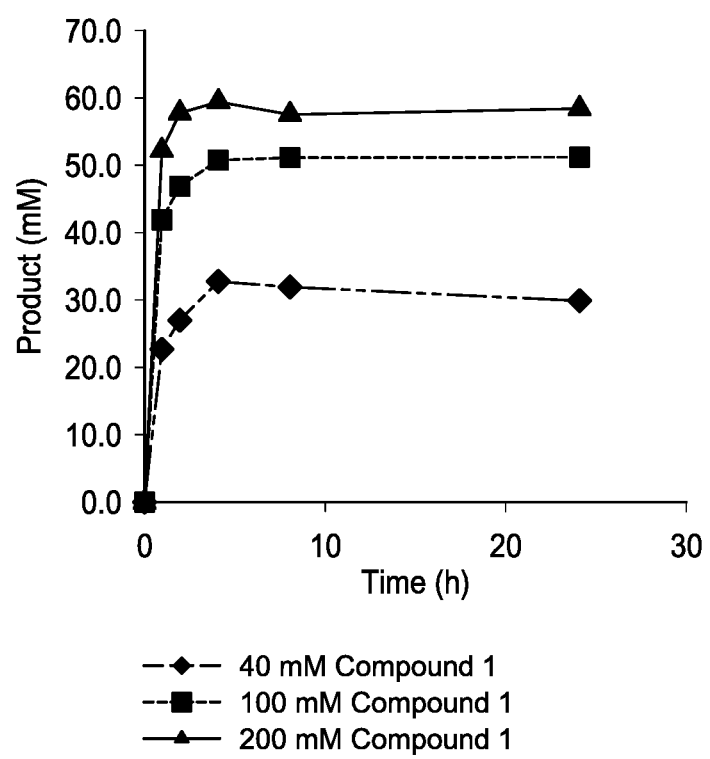

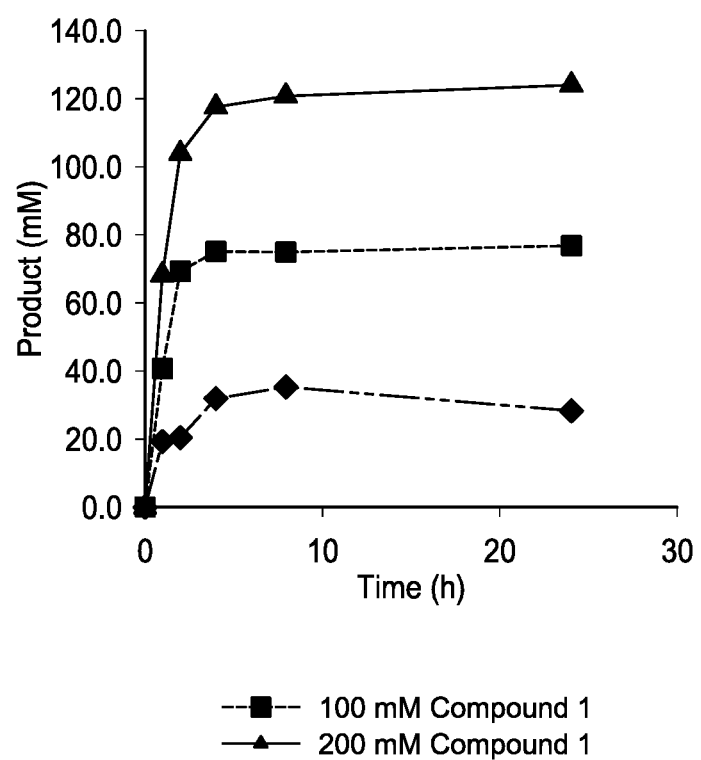

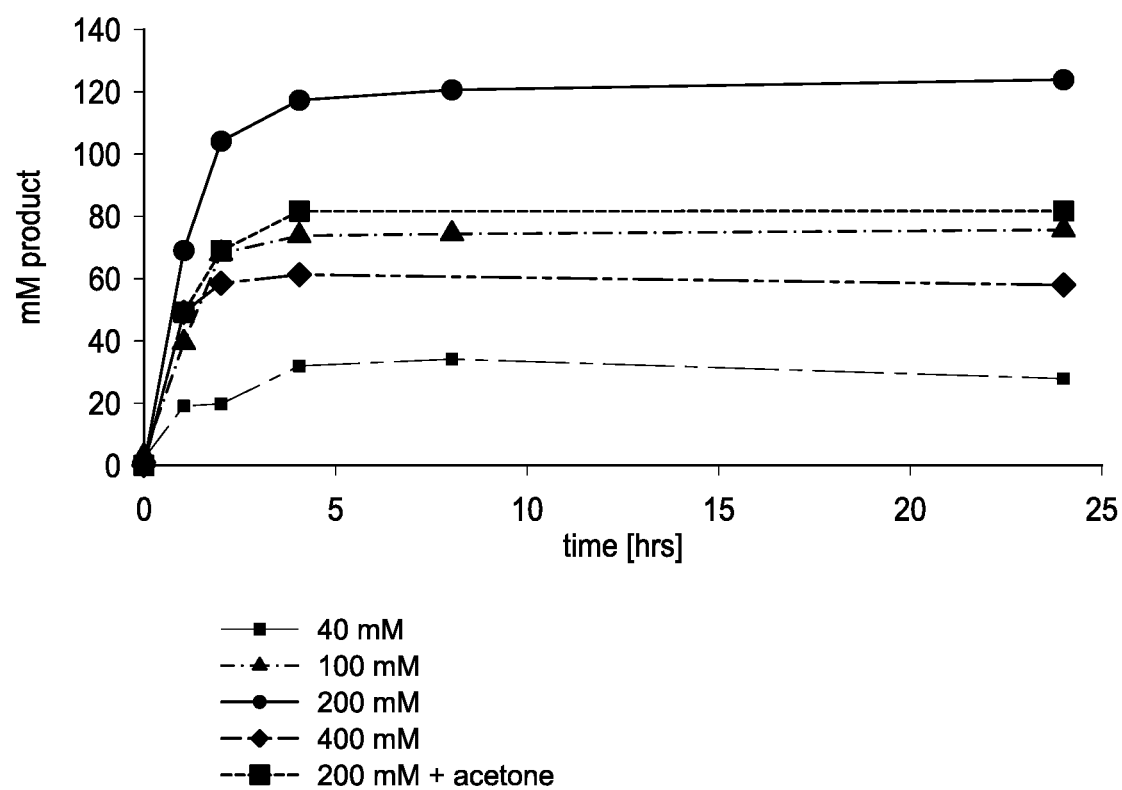

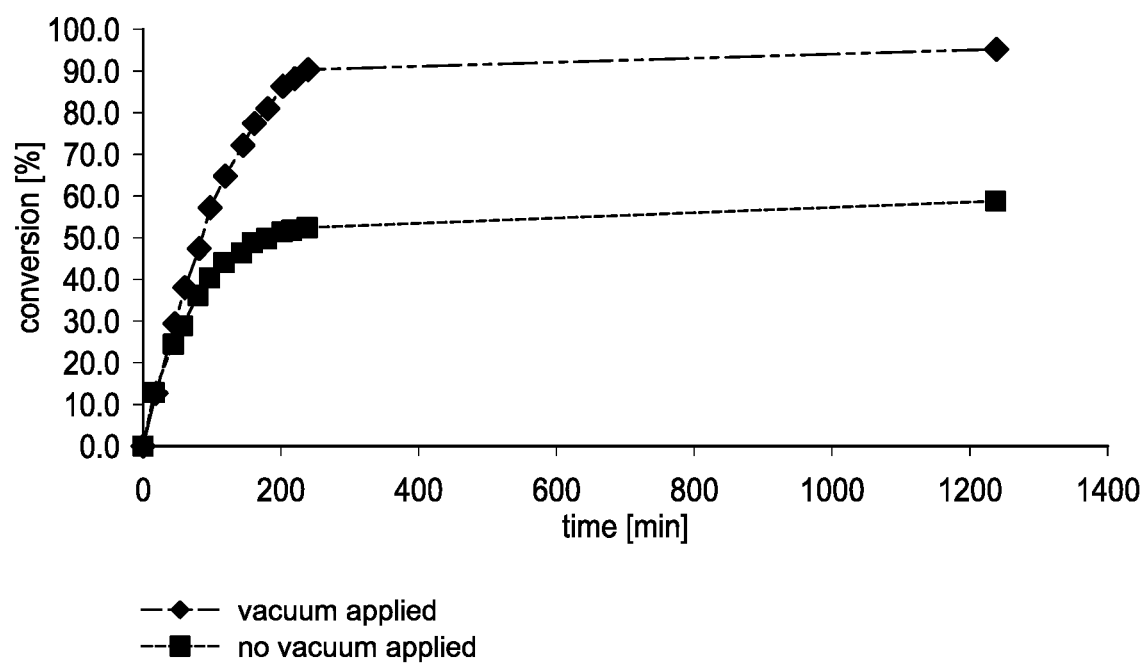

SYNTHESIS OF BORONATE ESTER DERIVATIVES AND USES THEREOF

INCORPORATION BY REFERENCE TO ANY PRIORITY APPLICATIONS

This application is a U.S. National Stage application under 35 U.S.C. § 371 of International Patent Application No. PCT/US2018/058143, filed Oct. 30, 2018, which claims the benefit of U.S. Provisional Application No. 62/580,343, filed Nov. 1, 2017, the disclosures of both of which are incorporated by reference in their entireties.

BACKGROUND

Field

The present application relates to certain compounds and to methods for the preparation of certain compounds that can be used in the fields of chemistry and medicine. More specifically, the present application relates to intermediates and methods in the synthesis of boronic acid antimicrobial compounds.

Description of the Related Art

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of anti-bacterial therapy. The increase in antibiotic resistant strains has been particularly common in major hospitals and care centers. The consequences of the increase in resistant strains include higher morbidity and mortality, longer patient hospitalization, and an increase in treatment costs.

Various bacteria have evolved β-lactam deactivating enzymes, namely, β-lactamases, that counter the efficacy of the various β-lactam antibiotics. β-lactamases can be grouped into 4 classes based on their amino acid sequences, namely, Ambler classes A, B, C, and D. Enzymes in classes A, C, and D include active-site serine β-lactamases, and class B enzymes, which are encountered less frequently, are Zn-dependent. These enzymes catalyze the chemical degradation of β-lactam antibiotics, rendering them inactive. Some β-lactamases can be transferred within and between various bacterial strains and species. The rapid spread of bacterial resistance and the evolution of multi-resistant strains severely limits β-lactam treatment options available.

The increase of class D β-lactamase-expressing bacterium strains such as *Acinetobacter baumannii* has become an emerging multidrug-resistant threat. *A. baumannii* strains express A, C, and D class β-lactamases. The class D β-lactamases such as the OXA families are particularly effective at destroying carbapenem type β-lactam antibiotics, e.g., imipenem, the active carbapenems component of Merck's Primaxin® (Montefour, K.; et al. Crit. Care Nurse 2008, 28, 15; Perez, F. et al. Expert Rev. Anti Infect. Ther. 2008, 6, 269; Bou, G.; Martinez-Beltran, J. Antimicrob. Agents Chemother. 2000, 40, 428. 2006, 50, 2280; Bou, G. et al, J. Antimicrob. Agents Chemother. 2000, 44, 1556). This has imposed a pressing threat to the effective use of drugs in that category to treat and prevent bacterial infections. Indeed the number of catalogued serine-based β-lactamases has exploded from less than ten in the 1970s to over 300 variants. These issues fostered the development of five "generations" of cephalosporins. When initially released into clinical practice, extended-spectrum cephalosporins resisted hydrolysis by the prevalent class A β-lactamases, TEM-1 and SHV-1. However, the development of resistant strains by the evolution of single amino acid substitutions in TEM-1 and SHV-1 resulted in the emergence of the extended-spectrum β-lactamase (ESBL) phenotype.

New β-lactamases have recently evolved that hydrolyze the carbapenem class of antimicrobials, including imipenem, biapenem, doripenem, meropenem, and ertapenem, as well as other β-lactam antibiotics. These carbapenemases belong to molecular classes A, B, and D. Class A carbapenemases of the KPC-type predominantly in *Klebsiella pneumoniae* but now also reported in other Enterobacteriaceae, *Pseudomonas aeruginosa* and *Acinetobacter baumannii*. The KPC carbapenemase was first described in 1996 in North Carolina, but since then has disseminated widely in the US. It has been particularly problematic in the New York City area, where several reports of spread within major hospitals and patient morbidity have been reported. These enzymes have also been recently reported in France, Greece, Sweden, United Kingdom, and an outbreak in Germany has recently been reported. Treatment of resistant strains with carbapenems can be associated with poor outcomes.

Another mechanism of β-lactamase mediated resistance to carbapenems involves combination of permeability or efflux mechanisms combined with hyper production of beta-lactamases. One example is the loss of a porin combined in hyperproduction of ampC beta-lactamase results in resistance to imipenem in *Pseudomonas aeruginosa*. Efflux pump over expression combined with hyperproduction of the ampC β-lactamase can also result in resistance to a carbapenem such as meropenem.

Thus, there is a need for improved β-lactamase inhibitors and efficient methods for making these improved β-lactamase inhibitors.

SUMMARY

Some embodiments relate to a compound having the structure of Formula (I):

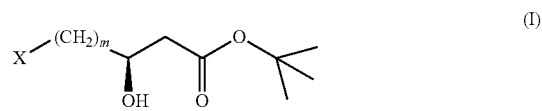

or a salt thereof, wherein X is a halogen and m is an integer between 2 and 6.

Some embodiments relate to a compound having the structure of Formula (II):
or a salt thereof, wherein:

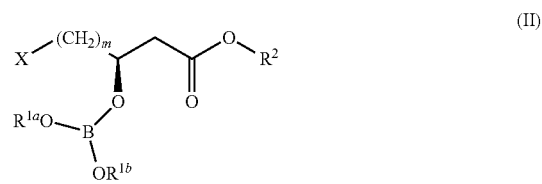

X is halogen, m is an integer between 2 and 6, each of $R^{1a}$ and $R^{1b}$ is independently selected from the group consisting of an optionally substituted $C_1$-$C_2$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl and optionally substituted heteroaryl, or $R^{1a}$ and $R^{1b}$ together with intervening atoms optionally form a 5-7 membered boron ester ring, and $R^2$ is selected from the group consisting of an optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl and optionally substituted heteroaryl.

Some embodiments relate to a method of making a compound of Formula (B), comprising the steps of:

reducing the ketone group of the keto-ester compound of Formula (A):

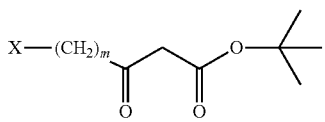

(A)

to form a compound of Formula (B):

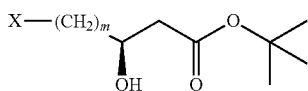

(B)

wherein:

X is a halogen, and m is an integer between 2 and 6.

Some embodiments relate to A method of making a compound of Formula (C), comprising:

reacting a boronate compound $B(OR^{4a})(OR^{4b})(OR^{4c})$ with a compound of Formula (B-1)

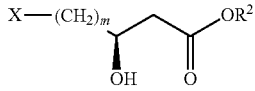

(B-1)

to form the compound of Formula (C)

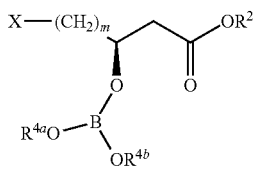

(C)

wherein:

X is a halogen, m is an integer between 2 and 6, $R^2$ is selected from the group consisting of an optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl and optionally substituted heteroaryl, and $R^{4a}$ and $R^{4b}$ are independently selected from the group consisting of an optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl and optionally substituted heteroaryl, or $R^{4a}$ and $R^{4b}$ together with intervening atoms optionally form a 5-8 membered boron ester ring; and $R^{4c}$ is selected from the group consisting of an optionally substituted $C_1$-$C_2$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl and optionally substituted heteroaryl.

Some embodiments relate to a method of making a compound of Formula (D), comprising:

reacting magnesium with a compound of Formula (C):

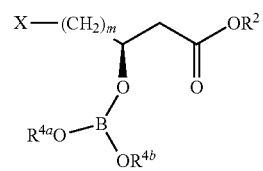

(C)

to form a first reaction intermediate, and hydrolyzing the first reaction intermediate to form the compound of Formula (D):

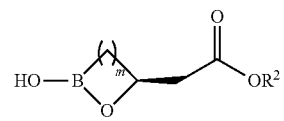

(D)

wherein:

X is a halogen, m is an integer between 2 and 6, and $R^2$ is selected from the group consisting of an optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl and optionally substituted heteroaryl, and each of $R^{4a}$ and $R^{4b}$ are independently selected from the group consisting of an optionally substituted $C_1$-$C_2$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl and optionally substituted heteroaryl, or $R^{4a}$ and $R^{4b}$ together with intervening atoms optionally form a 5-8 membered boron ester ring.

Some embodiments relate to a method of making a compound of Formula (E), comprising reducing the ketone group of a keto-ester compound of Formula (A-1),

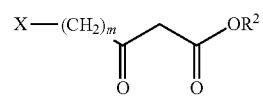

(A-1)

to form a compound of Formula (B-1),

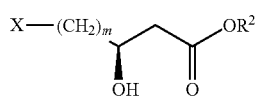
(B-1)

reacting a boronate compound B(OR$^{4a}$)(OR$^{4b}$)(OR$^{4c}$) with the compound of Formula (B-1) to form a compound of Formula (C),

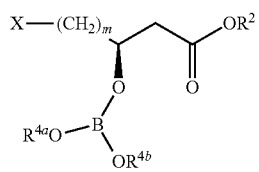
(C)

reacting magnesium with the compound of Formula (C) to form a first reaction intermediate,
hydrolyzing the first reaction intermediate to form a compound of Formula (D),

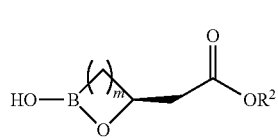
(D)

reacting the compound of Formula (D) with a complexing agent of Formula (CL)

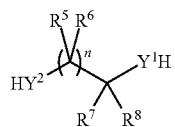
(CL)

to form the compound of Formula (E):

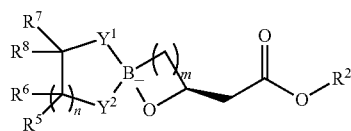
(E)

wherein:
X is a halogen,
m is an integer between 2 and 6,
n is an integer between 0 and 6,
$Y^1$ is O or $N^+R^9R^{10}$,
$Y^2$ is O or $NR^1$;
$R^2$ is selected from the group consisting of an optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl and optionally substituted heteroaryl, and each $R^5$ and $R^6$ are independently selected from the group consisting of H, optionally substituted phenyl and optionally substituted $C_{1-4}$ alkyl, or $R^5$ and $R^6$ together with the atom to which they are attached, form =O;
each $R^7$ and $R^8$ are independently selected from the group consisting of H, optionally substituted phenyl and optionally substituted $C_{1-4}$ alkyl, or $R^5$ and $R^7$ together with the atom to which they are attached form an aryl or heteroaryl ring; or $R^7$ and $R^8$ together with the atom to which they are attached, form =O; and
each $R^9$, $R^{10}$, and $R^{11}$ are independently selected from the group consisting of H, optionally substituted phenyl and optionally substituted $C_{1-4}$ alkyl.

BRIEF DESCRIPTION OF THE DRAWINGS

FIG. 1 shows the bioreduction of Compound 1 using an alcohol dehydrogenase system at pH 6.5 and pH 7.5.
FIG. 2 shows the bioreduction reaction progress with a GDH/glucose regeneration system.
FIG. 3 shows the bioreduction reaction progress with an IPA system.
FIG. 4 shows the effect of acetone on the reduction of Compound 1.
FIG. 5 shows the effect of acetone removal on the reduction reaction of Compound 1.

DETAILED DESCRIPTION OF THE PREFERRED EMBODIMENT

Numerous references are cited herein. The references cited herein, including the U.S. patents cited herein, are each to be considered incorporated by reference in their entirety into this specification.

Embodiments of the invention include, but are not limited to, methods for the preparation of various compounds and intermediates, and the compounds and intermediates themselves. In some embodiments, one or more substituents, one or more compounds, or groups of compounds can be specifically excluded in any one or more of the methods or compounds as described more fully below.

Where the compounds disclosed herein have at least one chiral center, they may exist as individual enantiomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein. Additionally, in some embodiments, the compounds disclosed herein can form oligomers and other higher-order polymers.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Definitions

As used herein, abbreviations of the ligand are defined as follows.
(S)-BINA=(S)-Biphenylindanone A
(R)-BINAP=(R)-(+)-2,2'-Bis(diphenylphosphino)-1,1'-binaphthyl
(R)—$H_8$-BINAP=(R)-(+)-2,2'-Bis(diphenylphospino)-5,5',6,6',7,7',8,8'-octahydro-1,1'-binaphthyl
(R)-SegPhos=(R)-(+)-5,5'-Bis(diphenylphosphino)-4,4'-bi-1,3-benzodioxole
(R)-DM-SegPhos=(R)-(+)-5,5'-Bis[di(3,5-xylyl)phosphino]-4,4'-bi-1,3-benzodioxole
(S)-SegPhos=(S)-(−)-5,5'-Bis(diphenylphosphino)-4,4'-bi-1,3-benzodioxole
(R)-tolyl-BINAP=(R)-(+)-2,2'-Bis(di-p-tolylphosphino)-1,1'-binaphthyl
(R)-xylyl-BINAP=(R)-(+)-2,2'-bis(di(3,5-xylyl)phosphino)-1,1'-binaphthy
(S)-tolyl-BINAP=(S)-(−)-2,2'-p-tolyl-phosphino)-1,1'-binaphthyl
(S)-BINAPHANE=(R,R)-1,2-Bis[(R)-4,5-dihydro-3H-binaphtho(1,2-c:2',1'-e)phosphepino]benzene
(S)-PhanePhos=(S)-(+)-4,12-Bis(diphenylphosphino)-[2.2]-paracyclophane
JosiPhos-2-1=(R)-1-[(SP)-2-(Diphenylphosphino)ferrocenyl]ethyldi-tert-butylphosphine
(R)-SolPhos SL-A001-1=(R)-7,7'-Bis(diphenylphosphino)-3,3',4,4'-tetrahydro-4,4'-dimethyl-8,8'-bi(2H-1,4-benzoxazine)
(S)-MeOBiPhep=(S)-(−)-2,2'-Bis(diphenylphosphino)-6,6'-dimethoxy-1,1'-biphenyl,
(S)—P-Phos=(S)-(−)-2,2',6,6'-Tetramethoxy-4,4'-bis(diphenylphosphino)-3,3'-bipyridine
(S)-(+)-DTBM-SEGPHOS=(S)-(+)-5,5'-Bis[di(3,5-di-tert-butyl-4-methoxyphenyl)phosphino]-4,4'-bi-1,3-benzodioxole "Solvate" refers to the compound formed by the interaction of a solvent and a compound described herein or salt thereof. Suitable solvates are pharmaceutically acceptable solvates including hydrates.

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_4$-10 (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "oxo" refers to =O.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—N(R$_A$)SO$_2$R$_B$" group in which R$_A$ and R$_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—OC(=O)NR$_A$R$_B$" group in which R$_A$ and R$_B$ are each independently selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 5-10 membered heterocyclyl, as defined herein.

An "N-carbamyl" group refers to an "—N(R$_A$)C(=O)OR$_B$" group in which R$_A$ and R$_B$ are each independently selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 5-10 membered heterocyclyl, as defined herein.

An "O-thiocarbamyl" group refers to a "—OC(=S)NR$_A$R$_B$" group in which R$_A$ and R$_B$ are each independently selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 5-10 membered heterocyclyl, as defined herein.

An "N-thiocarbamyl" group refers to an "—N(R$_A$)C(=S)OR$_B$" group in which R$_A$ and R$_B$ are each independently selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 5-10 membered heterocyclyl, as defined herein.

A "C-amido" group refers to a "—C(=O)NR$_A$R$_B$" group in which R$_A$ and R$_B$ are each independently selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 5-10 membered heterocyclyl, as defined herein.

An "N-amido" group refers to a "—N(R$_A$)C(=O)R$_B$" group in which R$_A$ and R$_B$ are each independently selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 5-10 membered heterocyclyl, as defined herein.

An "amino" group refers to a "—NR$_A$R$_B$" group in which R$_A$ and R$_B$ are each independently selected from hydrogen, C$_{1-6}$ alkyl, C$_{2-6}$ alkenyl, C$_{2-6}$ alkynyl, C$_{3-7}$ carbocyclyl, C$_{6-10}$ aryl, 5-10 membered heteroaryl, and 5-10 membered heterocyclyl, as defined herein. A non-limiting example includes free amino (i.e., —NH$_2$).

An "aminoalkyl" group refers to an amino group connected via an alkylene group.

An "alkoxyalkyl" group refers to an alkoxy group connected via an alkylene group, such as a "C$_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substitutents independently selected from C$_1$-C$_6$ alkyl, C$_1$-C$_6$ alkenyl, C$_1$-C$_6$ alkynyl, C$_1$-C$_6$ heteroalkyl, C$_3$-C$_7$ carbocyclyl (optionally substituted with halo, C$_1$-C$_6$ alkyl, C$_1$-C$_6$ alkoxy, C$_1$-C$_6$ haloalkyl, and C$_1$-C$_6$ haloalkoxy), C$_3$-C$_7$-carbocyclyl-C$_1$-C$_6$-alkyl (optionally substituted with halo, C$_1$-C$_6$ alkyl, C$_1$-C$_6$ alkoxy, C$_1$-C$_6$ haloalkyl, and C$_1$-C$_6$ haloalkoxy), 5-10 membered heterocyclyl (optionally substituted with halo, C$_1$-C$_6$ alkyl, C$_1$-C$_6$ alkoxy, C$_1$-C$_6$ haloalkyl, and C$_1$-C$_6$ haloalkoxy), 5-10 membered heterocyclyl-C$_1$-C$_6$-alkyl (optionally substituted with halo, C$_1$-C$_6$ alkyl, C$_1$-C$_6$ alkoxy, C$_1$-C$_6$ haloalkyl, and C$_1$-C$_6$ haloalkoxy), aryl (optionally substituted with halo, C$_1$-C$_6$ alkyl, C$_1$-C$_6$ alkoxy, C$_1$-C$_6$ haloalkyl, and C$_1$-C$_6$ haloalkoxy), aryl(C$_1$-C$_6$)alkyl (optionally substituted with halo, C$_1$-C$_6$ alkyl, C$_1$-C$_6$ alkoxy, C$_1$-C$_6$ haloalkyl, and C$_1$-C$_6$ haloalkoxy), 5-10 membered heteroaryl (optionally substituted with halo, C$_1$-C$_6$ alkyl, C$_1$-C$_6$ alkoxy, C$_1$-C$_6$ haloalkyl, and C$_1$-C$_6$ haloalkoxy), 5-10 membered heteroaryl(C$_1$-C$_6$) alkyl (optionally substituted with halo, C$_1$-C$_6$ alkyl, C$_1$-C$_6$ alkoxy, C$_1$-C$_6$ haloalkyl, and C$_1$-C$_6$ haloalkoxy), halo, cyano, hydroxy, C$_1$-C$_6$alkoxy, C$_1$-C$_6$ alkoxy(C$_1$-C$_6$)alkyl (i.e., ether), aryloxy, sulfhydryl (mercapto), halo(C$_1$-C$_6$) alkyl (e.g., —CF$_3$), halo(C$_1$-C$_6$)alkoxy (e.g., —OCF$_3$), C$_1$-C$_6$ alkylthio, arylthio, amino, amino(C$_1$-C$_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

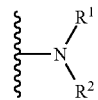

and R$^1$ and R$^2$ are defined as selected from the group consisting of hydrogen and alkyl, or R$^1$ and R$^2$ together with the nitrogen to which they are attached form a heteroaryl, it is meant that R$^1$ and R$^2$ can be selected from hydrogen or alkyl, or alternatively, the substructure has structure:

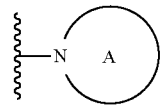

where ring A is a heteroaryl ring containing the depicted nitrogen.

Similarly, when two "adjacent" R groups are said to form a ring "together with the atoms to which they are attached," it is meant that the collective unit of the atoms, intervening bonds, and the two R groups are the recited ring. For example, when the following substructure is present:

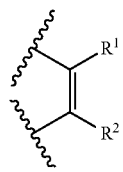

and R$^1$ and R$^2$ are defined as selected from the group consisting of hydrogen and alkyl, or R$^1$ and R$^2$ together with the atoms to which they are attached form an aryl or carbocyclyl, it is meant that $R^1$ and $R^2$ can be selected from hydrogen or alkyl, or alternatively, the substructure has structure:

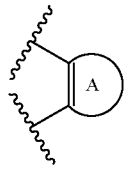

where A is an aryl ring or a carbocyclyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

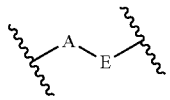

includes the substituent being oriented such that the A is attached at the leftmost attachment point of the molecule as well as the case in which A is attached at the rightmost attachment point of the molecule.

"Leaving group," or "LG," as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in Organic Chemistry, 2d ed., Francis Carey (1992), pages 328-331; Introduction to Organic Chemistry, 2d ed., Andrew Streitwieser and Clayton Heathcock (1981), pages 169-171; and Organic Chemistry, 5th ed., John McMurry (2000), pages 398 and 408; all of which are incorporated herein by reference for the limited purpose of disclosing characteristics and examples of leaving groups.

Unless defined otherwise, all technical and scientific terms used herein have the same meaning as commonly understood by one of ordinary skill in the art to which the embodiments belong. Although any methods and materials similar or equivalent to those described herein can also be used in the practice or testing of the embodiments, the preferred methods and materials are now described. All publications mentioned herein are incorporated herein by reference to disclose and describe the methods and/or materials in connection with which the publications are cited.

Protecting Groups

In some circumstances, a chemical reaction may need to be performed selectively at one reactive site in a multifunctional compound. One such method that is useful for accomplishing such selectivity is to temporarily block one or more reactive sites in the multifunctional compound with a protective group. Such a method is often referred to as "protecting" the functional group. Many protecting groups are known in the art. See, e.g., Greene et al., Protective Groups in Organic Synthesis, Third Ed. (John Wiley & Sons, Inc. 1999), herein incorporated by reference in its entirety; Wutz et al., Greene's Protective Groups in Organic Synthesis, Fourth Ed. (John Wiley & Sons, Inc. 2007), herein incorporated by reference in its entirety. When more than one reactive site in a multifunctional compound requires protecting, or when a compound is prepared that will possess more than one protected functional group, it is important to use orthogonal protecting groups. Protecting groups are orthogonal if they are susceptible to selective removal.

In some embodiments, it may be necessary to protect one or more functional groups so as to prevent their interference in the desired reaction. For example, it may be necessary to protect one or more functional groups such as amines, carboxylic acids, and/or hydroxyl groups.

Suitable protecting groups for protecting amines include: carbamates such as alkyl carbamates including methyl; ethyl, propyl, isopropyl, butyl, tert-butyl, sec-butyl, pentyl, neopentyl, hexyl, heptyl, nonnyl, decanyl, and configurational isomers thereof; 9-flurenylmethyl; 9-(2-sulfo)flurenylmethyl; 9-(2,7-dibromo)fluorenylmethyl; 17-tetrabenzo[a,c,g,i]flurenylmethyl; 2-chloro-3-indenylmethyl; benz[f]inden-3-ylmethyl; 2,7-di-t-butyl[9-(10,10-dioxo-10,10,10,10-tetrahydrothioxanthyl)]methyl; 1,1-dioxobenzo[b]thiophene-2-ylmethyl; substituted ethyl carbamates such as 2,2,2-trichloroethyl; 2-trimethylsilylethyl; 2-phenylethyl; 1-(1-adamantyl)-1-methylethyl; 2-chloroethyl; 1,1-dimethyl-2-haloethyl; 1,1-dimethyl,2,2-dibromoethyl; 1,1-dimethyl-2,2,2-trichloroethyl; 1-methyl-1-(4-biphenylyl)ethyl; 1-(3,5-di-t-butylphenyl)-1-methylethyl; 2-(2'- and 4'-prydyl)ethyl; N-(2-pivaloylamino)-1,1-dimethylethyl; 2-[(2-nitrophenyl)dithio]-1-phenylethyl; 2-(N,N,-dicyclohexylcarboxamido)ethyl; t-butyl; 1-adamantyl; 2-adamantyl; vinyl; allyl; 1-isopropylallyl; cinnamyl; 4-nitrocinnamyl; 3-(3'-pyridyol)prop-2-enyl; 8-quinolyl; N-hydroxypiperidinyl; alkyldithio; benzyl; p-methoxybenzyl; p-nitrobenzykl; p-bromobenzyl; p-chlorobenzyl; 2,4-dichlorobenzyl; 4-methylsulfinylbenzyl; 9-anthrylmethyl; diphenylmethyl; 2-methylthioethyl; 2-methylsulfonylethyl; 2-(p-toluenesulfonyl)ethyl; [2-(1,3-dithianyl)]methyl; 4-methylthiophenyl; 2,4-dimethylthiophenyl; 2-phosphonioethyl; 1-methyl-1-(triphenylphosphonio)ethyl; 1,1-dimethyl-2-cyanoethyl; 2-dansylethyl; 2-(4-nitrophenyl)ethyl; 4-phenylacetoxybenzyl; 4-azidobenzyl; 4-azidomethoxybenzyl; m-chloro-p-acyloxybenzyl; p-(dihydroxyboryl)benzyl; 5-benzisoxazolylmethyl; 2-(trifluoromethyl)-6-chromonylmethyl; m-nitrophenyl; 3,5-dimethoxybenzyl; 1-methyl-1-(3,5-dimethoxyphenyl)ethyl; α-methylnitropiperonyl; o-nitrobenzyl; 3,4-dimethoxy-6-nitrobenzyl; phenyl(o-nitrophenyl)methyl; 2-(2-nitrophenyl)ethyl; 6-nitroveratryl; 4-methoxyphenacyl; 3',5'-dimethoxybenzoin; phenothiazinyl-(10)-carbonyl derivatives; N'-p-toluenesulfonylaminocarbonyl; N'-phenylaminothiocarbonyl; t-amyl; S-benzyl thiocarbamate; butynyl; p-cyanobenzyl; cyclobutyl; cyclohexyl; cyclopentyl; cyclopropylmethyl; p-dicyloxybenzyl; diisopropylmethyl; 2,2-dimethoxycarbonylvinyl; o-(N',N'-dimethylcarboxamido)benzyl; 1,1-dimethyl-3-(N',N'-dimethylcarboxamido)propyl; 1,1-dimethylpropynyl; di(2-pyridyl)methyl; 2-furanylmethyl; 2-iodoethyl; isobornyl; isobutyl; isonicotinyl; p-(p'-methoxyphenylazo)benzyl; 1-methylcyclobutyl; 1-methylcyclohexyl; 1-methyl-1-cyclopropylmethyl; 1-methyl-1-(p-phenylazophenyl)ethyl; 1-methyl-1-phenylethyl; 1-methyl-1-(4'-pyridyl)ethyl; phenyl; p-(phenylazo)benzyl; 2,4,6-tri-t-butylphenyl; 4-(trimethylammonium)benzyl; 2,4,6-trimethylbenzyl; and other similar carbamates; amides, including, but not limited to, formyl, acetyl, chloroacetyl, trichloroacetyl, trifluoroacetyl, phenylacetyl, propionyl, 3-phenylpropionyl, 4-pentenoyl, picolinoyl, 3-pyridylcarboxamide, benzoylphenylalanyl, benzoyl, p-phenylbenzoyl, amides whose cleavage is induced by nitro group reduction, such as o-nitrophenylacetyl, o-nitrophenoxyacetyl, 3-(o-nitrophenyl)propionyl, 2-methyl-2-(o-nitrophenoxy)propionyl, 3-methyl-3-nitrobutyryl, o-nitrocinnamoyl, o-nitrobenzoyl, and 3-(4-t-butyl-2, 6-dinitrophenyl)-2,2-dimethylpropionyl; amides whose cleavage is induced by release of an alcohol, such as o-(benzoyloxymethyol)benzoyl, (2-acetoxymethyl)benzoyl, 2-[(t-butyldiphenylsiloxy)methyl]benzoyl, 3-(3',6'-dioxo-2', 4',5'-trimethylcyclohexa-1',4'-diene-3,3-dimethylpropionyl, and o-hydroxy-trans-cinnamoyl; amides whose cleavage is induced by other chemical reactions, such as 2-methyl-2-(o-phenylazophenoxy)propionyl, 4-chlorobutyryl, acetoacetyl, 3-(p-hydroxyphenyl)propionyl, (N'-dithiobenzyloxycarbonylamino)acetyl, N-acetylmethionine, and 4,5-diphenyl-3-oxazolin-2-one; cyclic imide derivatives such as N-phthaloyl, N-tetrachlorophthaloyl, N-4-nitrophthaloyl, N-dithiasuccinoyl, N-2,3-diphenylmaleoyl, N-2,5-dimethylpyrrolylN-2,5-bis(triisopropylsiloxy)pyrrolyl, N-1,1,4,4,-tetramethyldisilylazacyclopentane adduct, N-1,1,3,3,-tetramethyl-1,3-disilaisoindolyl, 5-substituted 1,3-dimethyl-1, 3,5-triazacyclohexan-2-one, 5-substituted 1,3-dibenzyl-1,3, 5-triazacyclohexan-2-one, 1-substituted 3,5-dinitro-4-pyridonyl, and 1,3,5-dioxazinyl; N-alkyl and N-aryl derivatives, such as N-methyl, N-t-butyl, N-allyl, N-[2-(trimethylsilyl)ethoxy]methyl, N-3-acetoxypropyl, N-cyanomethyl, N-(1-isopropyl-4-nitro-2-oxo-3-pyrrolin-3-yl), N-2,4-dimethoxybenzyl, N-2-azanorbornenyl, N-2,4-dinitrophenyl, quaternary ammonium salts, N-benzyl, N-4-methoxybenzyl, N-2,4-dimethoxybenzyl, N-2-hydroxybenzyl, N-diphenylmethyl, N-bis(4-methoxyphenyl)methyl, N-5-dibenzosuberyl, N-triphenylmethyl, N-(4-methoxyphenyl)duiphenylmethyl, N-9-phenylfluorenyl, N-ferrocenylmethyl, and N-2-picolylamine N'-oxide; imine derivatives, such as N-1,1-dimethylthiomethylene, N-benzylidene, N-p-methoxybenzylidine, N-diphenylmethylene, N-[(2-pyridyl)mesityl]methylene, N—(N',N'-dimethylaminomethylene), N—(N',N'-dibenzylaminomethylene), N—(N'-t-butylaminomethylene), N,N'-isopropylidene, N-p-nitrobenzylidene, N-salicylidene, N-5-chlorosalicylidene, N-(5-chloro-2-hydroxyphenyl)phenylmethylene, N-cyclohexylidene, and N-t-butylidene; enamine derivatives, such as N-(5,5-dimethyl-3-oxo-1-cyclohexenyl), N-2,7-dichloro-9-fluorenylmethylene, N-2-(4,4-dimethyl-2,6-dioxocyclohexylidene) ethyl, N-4,4,4-trifluoro-3-oxo-1-butenyl, and N-1-isopropyl-4-nitro-2-oxo-3-pyrrolin-3-yl; and N-heteroatom derivatives such as N-metal, N-borane, N-diphenylborinic acid, N-diethylborinic acid, N-difloroborinic acid, N,N'-3, 5-bis(trifluoromethyl)phenylboronic acid, N-[phenyl(pentacarbonylchromium-or-tungsten)]carbonyl, N-copper chelates, N-zinc chelates, and 18-crown-6 derivatives, N—N derivatives such as N-nitro, N-nitroso, N-oxide, and triazene derivatives, N—P derivatives such as N-diphenylphosphinyl, N-dimethylthiophosphinyl, N-diphenylthiophosphinyl, N-dialkylphosphoryl, N-dibenzylphosphoryl, N-diphenylphosphoryl, and iminotriphenylphosphorane derivatives, N—Si derivatives, N-sulfenyl derivatives such as N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-1-(2,2,2-trifluoro-1,1-diphenyl)ethylsulfenyl, and N-3-nitro-2-pyridinesulfenyl, and/or N-sulfonyl derivatives such as N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5, 6-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-3-methoxy-4-t-butylbenzenesulfonyl, N-2,2,5,7,8-pentamethylchroman-6-sulfonyl, N-2-nitrobenzenesulfonyl, N-4-nitrobenzenesulfonyl, N-2,4-dinitrobenzenesulfonyl, N-benzothiazole-2-sulfonyl, N-methanesulfonyl, N-2-(trimethylsilyl)ethanesulfonyl, N-9-anthracenesulfonyl, N-4-(4', 8'-dimethoxynaphthylmethyl)benzenesulfonyl, N-benzylsulfonyl, N-trifluoromethylsulfonyl, N-phenacylsulfonyl, and N-t-butylsulfonyl.

Suitable protecting groups for carboxylic acids include: esters such as enzymatically cleavable esters including heptyl, 2-N-(morpholino)ethyl, choline, (methoxyethoxy)ethyl, methoxyethyl; alkyl esters such as methyl, ethyl, propyl, isopropyl, butyl, tert-butyl, sec-butyl, pentyl, neopentyl, hexyl, heptyl, nonnyl, decanyl, and configurational isomers thereof; substituted methyl esters such as 9-fluroenylmethyl, methoxymethyl, methylthiomethyl, tetrahydropyranyl, teatrahydrofuranyl, methoxyethoxymethyl, 2-(trimethylsilyl)ethoxymethyl, benzyloxymethyl, pivaloyloxymethyl, phenylacetoxymethyl, triisopropylsilylmethyl, cyanomethyl, acetol, phencacyl, p-bromophenacyl, α-methylphenacyl, p-methoxyphenacyl, desyl, carboamidomethyl, p-azobenzenecarboxamidomethyl, N-phthalidimdomethyl; 2-substituted ethyl esters such as 2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl) ethyl, 2-(p-toluenesulfonyl)ethyl, 2-(2'-pyridyl)ethyl, 2-(p-methoxyphenyl)ethyl, 2-(diphenylphosphino)ethyl, 1-methyl-1-phenylethyl, 2-(4-acetyl-2-nitrophenyl)ethyl, 2-cyanoethyl, 3-methyl-3-pentyl, dicyclopropylmethyl, 2,4-dimethyl-3-pentyl, cyclopentyl, cyclohexyl, allyl, methallyl, 2-methylbut-e-en-2-yl, 3-methylbut-2-(prenyl), 3-buten-1-yl, 4-(trimethylsilyl)-2-buten-1-yl, cinnamyl, α-methylcinnamyl, prop-2-ynyl, phenyl; 2,6-dialkylphenyl esters such as 2,6-dimethylphenyl, 2,6-diisopropylphenyl, 2,6-di-t-butyl-4-methylphenyl, 2,6-di-t-butyl-4-methoxyphenyl, p-(methylthio)phenyl, pentafluorophenyl, benzyl; substituted benzyl esters such as triphenylmethyl, diphenylmethyl, bis(o-mitrophenyl)methyl, 9-anthrylmethyl, 2-(9,10-dioxo)anthrylmethyl, 5-dibenzosuberyl, 1-pyreneylmethyl, 2-(trifluoromethyl)-6-chromonylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, 4-azidomethoxybenzyl, 4-{N-[1-(4,4-dimethyl-2,6-dioxocyclohexylidene)-3-methylbutyl] amino}benzyl, piperonyl, 4-picolyl, polymer supported p-benzyl; silyl esters such as trimethylsilyl, triethylsilyl, t-butyldimethylsilyl, i-propyldimethylsilyl, phenyldimethylsilyl, di-t-butylmethylsilyl, triisopropylsilyl; activated esters such as thiol esters; oxazoles; 2-alkyl-1,3-axazoline; 4-alkyl-5-oxo-1,3-oxazolidine; 2,2-bistrifluoromethyl-4-alkyl-5-oxo-1,3-oxazolidine; 5-alkyl-4-oxo-1,3-dioxolane; dioxanones; ortho esters; pentaaminocobalt(III) complexes; and stannyl esters such as triethylstannyl and tri-n-butylstannyl; amides such as N,N-dimethyl, pyrrolidinyl, piperidinyl, 5,6-dihydrophenanthridinyl, o-nitroanilide, N-7-nitroindolyl, N-8-nitro-1,2,3,4-tetrahydroquinolyl, 2-(2-aminophenyl)acetaldehyde dimethyl acetal amide, and polymer supported p-benzenesulfonamide; hydrazides such as N-phenyl, N,N'diisopropyl; and tetraalkylammonium salts such as methyl, ethyl, propyl, isopropyl, butyl, tert-butyl, sec-butyl, pentyl, neopentyl, hexyl, heptyl, nonnyl, decanyl, and configurational isomers thereof.

Suitable protecting groups for hydroxyl groups include: silyl ethers such as trimethylsilyl, triethylsilyl, triisopropylsilyl, dimethylisopropylsilyl, diethylisopropylsilyl, dimethylthexylsilyl, 2-norbornyldimethylsilyl, t-butyl-dimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl: sisyl; (2-hydroxystyryl)dimethylsilyl; (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, fluorous silyl; $C_{1-10}$alkyl ethers such as methyl, ethyl, propyl, isopropyl, butyl, tert-butyl, sec-butyl, pentyl, neopentyl, hexyl, heptyl, nonnyl, decanyl, and configurational isomers thereof; substituted methyl ethers such as methoxymethyl, methylthiomethyl, (phenyldimethylsilyl)methoxymethyl, benzyloxymethyl, p-methoxybenzyloxymethyl, [(3,4-dimethoxybenzyl)oxy]methyl, p-nitrobenzyloxymethyl, o-nitrobenzyloxymethyl, [(R)-1-(2-nitrophenyl)ethoxy]methyl, (4-methoxyphenoxy)methyl, guaiacolmethyl, t-butoxymethyl, 4-pentenyloxymethyl, siloxymethyl, 2-methoxyethoxymethyl, 2-cyanoethoxymethyl, 2,2,2-trichloroethoxymethyl, bis(2-chloroethoxy)methyl, 2-(trimethylsilyl)ethoxymethyl, methoxymethyl, O-Bis(2-acetoxyethoxy)methyl, tetrahydropyranyl, fluorous tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxide, 1-[(2-chloro-4-methyl)phenyl]-4-methoxypiperidin-4-yl, 1-(2-fluorophenyl)-4-methoxypiperidin-4-yl, 1-(4-chlorophenyl)-4-methoxypiperidin-4-yl, 1,4-dioxan-2-yl, tetrahydrofuranyl, tetrahydrothiofuranyl, and 2,3,2a,4,5,6,7,7a-octahydro-7,8,8-trimethyl-4,7-methanobenzofuran-2-yl; substituted ethyl ethers such as 1-ethoxyethyl, 1-(2-chloroethoxy)ethyl, 2-hyddroxyethyl, 2-bromoethyl, 1-[2-(trimethylsilyl)ethoxy]ethyl, 1-methyl-1-methoxyethyl, 1-methyl-lbenzyloxyethyl, 1-methyl-1-benzyloxy-2-fluoroethyl, 1-methyl-1-phenoxyethyl, 2,2,2-trichloroethyl, 1,1-dianisyl-2,2,2-trichloroethyl, 1,1,1,3,3,3-hexafluoro-2-phenylisopropyl, 1-(2-cyanoethoxy)ethyl, 2-trimethylsilylethyl, 2-(benzylthio)ethyl, 2-(phenylselenyl)ethyl, t-butyl, allyl, prennyl, cinnamyl, 2-phenallyl, propargy, p-chlorophenyl, p-methoxyphenyl, p-nitrophenyl, 2,4-dinitrophenyl, 2,3,5,6-tetrafluoro-4-(trifluoromethyl)phenyl; benzyl; substituted benzyl ethers such as p-methoxybenzyl, 3,4-dimethoxybenzyl, o-nitrobenzyl, p-nitrobenzyl, pentadienylnitrobenzyl, pentadienylnitropiperonyl, halobenzyl, 2,6-dichlorobenzyl, 2,4-dichlorobenzyl, p-cyanobenzyl, p-phenylbenzyl, 2,6-difluorobenzyl, fluorous benzyl, 4-fluorousalkoxybenzyl, trimethylsilylxylyl, 2-phenyl-2-propyl (Cumyl), p-acylaminobenzyl, p-azidobenzyl, 4-azido-3-chlorobenzyl, 2-trifluoromethylbenzyl, 4-trifluromethylbenzyl, p-(methylsulfinyl)benzyl, p-siletanylbenzyl, 4-acetoxybenzyl, 4-(2-trimethylsilyl)ethoxymethoxybenzyl, 2-napthylmethyl, 2-picolyl, 4-picolyl, 3-methyl-2-picolyl N-oxido, 2-quinolinylmethyl, 6-methoxy-2-(4-methylphenyl)-4-quinoemethyl, 1-pyrenylmethyl, diphenylmethyl, 4-methoxydiphenylmethyl, 4-phenyldiphenylmethyl, p,p'-dinitrobenzhydryl, 5-dibenzosuberyl, triphenylmethyl, α-napthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 4,4'-dimethoxy-3"-[N-imidazolylmethyl)]trityl, 4,4'-dimethoxy-3"-[N-imidazolylethyl)carbamoyl]trityl, 1,1-bis(4-methoxyphenyl)-1'-pyrenylmethyl, 4-(17-tetrabenzo[a,c,g,i]fluorenylmethyl)-4,4"-dimethoxytrityl, 9-anthryl, 9-(9-phenyl)xanthenyl, 9-phenylthioxanthyl, 9-(9-phenyl-10-oxo)anthryl, 1,3-benzodithiolan-2-yl, 4,5-bis(ethoxycarbonyl)-[1,3]-dioxolan-2-yl, benzisothiazolyl S,S-dioxido; $C_{1-10}$alkyl esters such as formyl, acetyl, propionyl, isopropionyl, butyryl, tert-butyryl, sec-butyryl, pentanoyl, neopentanoyl, hexanoyl, heptanoyl, nonanoyl, decanoyl, and configurational isomers thereof, esters such as benzoylformate, chloroacetate, dichloroacetate, trichloroacetate, trifluoroacetate, methoxyacetate, triphenylmethoxyacetate, phenoxyacetate, p-chlorophenoxyacetate, phenylacetate, polymer supported p-phenylacetate, diphenylacetate, bisfluorous chain type propanoyl, nicotinate, 3-phenylpropionate, 4-pentenoate, 4-oxopentanoate, 4,4-(ethylenedithio)pentanoate, 5-[3-bis(4-methoxyphenyl)hydroxymethylphenoxy]levulinate, pivaloate, 1-adamantoate, crotonate, 4-methoxycrotonate, benzoate, p-phenylbenzoate, 2,4,6-trimethylbenzoate, picolinate, nicotinate, 4-bromobenzoate, 2,5-difluorobenzoate, p-nitrobenzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, 2-methyl-2-butenoate, (E)-2-methyl-2-butenoate, (Z)-2-methyl-2-butenoate, o-(methoxycarbonyl)benzoate, polymer supported p-benzoate, α-naphthoate, nitrate, alkyl N,N, N',N'-tetramethylphosphorodiamidate, 2-chlorobenzoate, 3',5'-dimethoxybenzoin, N-phenylcarbamate, borate, dimethylphosphinothioyl, 2,4-dinitrophenylsulfenate, and photolabile esters; carbonates, including methyl, methoxymethyl, 9-fluorenylmethyl, ethyl, 2,2,2-trichloroethyl, 1,1-dimethyl-2,2,2-trichloroethyl, 2-(trimethylsilyl)ethyl, 2-(triphenylsulfonyl)ethyl, 2-(triphenylphosphonia)ethyl, isobutyl, vinyl, allyl, p-nitrophenyl, benzyl, p-methoxybenzyl, 3,3-dimethoxybenzyl, o-nitrobenzyl, p-nitrobenzyl, and silyl esters; carbonates cleaved by β-elimination such as 2-dansylethyl, 2-(4-nitrophenyl)ethyl, 2-(2,4-dinitrophenyl)ethyl, 2-cyano-1-phenylethyl, S-benzyl thiocarbonate, 4-ethoxy-1-mapthyl, and methyl dithiocarbonate, carbonates cleaved with assisted cleavage such as 2-iodobenzoate, 4-azidobutyrate, 4-nitro-4-methylpentanoate, o-(dibromomethyl)benzoate, 2-formylbenzenesulfonate, 2-(methylthiomethyoxy)ethyl, 4-(methylthiomethoxymethyl)butyrate, 2-(methylthiomethoxymethyl)benzoate, 2-(chloroacetoxymethyl)benzoate, 2-[(2-chloroacetoxy)ethyl]benzoate, 2-[2-(benzyloxy)ethyl]benzoate, 2-[2-(4-methoxybenzyloxy)ethyl]benzoate; and sulfonates such as sulfate, allylsulfate, $C_{1-10}$alkyl sulfonates such as methyl, ethyl, propyl, isopropyl, butyl, tert-butyl, sec-butyl, pentyl, neopentyl, hexyl, heptyl, nonnyl, decanyl, and configurational isomers thereof, benzylsulfonate, tosylate, and 2-[(4-nitrophenyl)ethyl]sulfonate.

Protection and Deprotection Reactions

Reagents, solvents, and reaction conditions useful for protecting amines, carboxylic acids, and alcohols are well-known in the art. Likewise, reagents, solvents, and reaction conditions useful for deprotecting amines, carboxylic acids, and alcohols are well known in the art. See, e.g., Greene et al., Protective Groups in Organic Synthesis, Third Ed. (John Wiley & Sons, Inc. 1999), herein incorporated by reference in its entirety; Wutz et al., Greene's Protective Groups in Organic Synthesis, Fourth Ed. (John Wiley & Sons, Inc. 2007), herein incorporated by reference in its entirety. While references have been made to specific reagents, solvents, and reaction conditions in the schemes described above, it is readily envisioned that equivalent reagents, solvents, and reaction conditions may be utilized to protect and deprotect amines, carboxylic acids, and alcohols.

Intermediate Compounds

Some embodiments disclosed herein include intermediates in the synthetic methods described herein, including a compound having the structure of Formula (I) or (II) as described herein.

In some embodiments, X is Cl. In some embodiments, m is 2.

In some embodiments for the compounds of Formula (II), X is a halogen, and each of $R^{1a}$ and $R^{1b}$ is independently selected from the group consisting of an optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl and optionally substituted heteroaryl, or $R^{1a}$ and $R^{1b}$ optionally form a 5-7 membered boron ester ring with intervening atoms, and $R^2$ is selected from the group consisting of an optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl and optionally substituted heteroaryl.

In some embodiments, X is Cl.

In some embodiments, each of $R^{1a}$ and $R^{1b}$ is a butyl group. In some embodiments, $R^{1a}$ and $R^{1b}$ are both n-butyl groups.

Methods of Preparation

Some embodiments relate to a method of making a compound of Formula (B) by reducing the ketone group of the keto-ester compound of Formula (A). In some embodiments, the reduction is performed using a Ruthenium based catalyst system. In some embodiments, the reduction is performed using an alcohol dehydrogenase bioreduction system In some embodiments, for the compound of Formula (A)-(C), (A-1), and (B-1), X is Cl. In some embodiments, m is 2.

In some embodiments, the ketone group in the compound of Formula (A) is reduced using a Ruthenium based catalyst.

In some embodiments, the Ruthenium based catalyst has the structure of Formula (III):

$$R^3Ru(X^1)_2 \quad (III),$$

wherein:
X$^1$ is a halogen, benzene, cymene, or an acetyl (OAc) group; and
R$^3$ is a ligand selected from the group consisting of (S)-BINA, (R)-BINAP, (R)—H$_8$-BINAP, (R)-SegPhos, (R)-DM-SegPhos, (S)-SegPhos, (R)-tolyl-BINAP, (R)-xylyl-BINAP, (S)-tolyl-BINAP, (S)-BINAPHANE, (S)-PhanePhos, JosiPhos-2-1, (R)-SolPhos SL-A001-1, (S)-MeOBiPhep, (S)—P-Phos, and (S)-(+)-DTBM-SEGPHOS.

In some embodiments, X$^1$ is a Cl or —OAc group.

In some embodiments, R$^3$ is (R)-SegPhos.

In some embodiments, the Ruthenium based catalyst is Ru(OAc)$_2$((R)-SegPhos).

In some embodiments, the Ruthenium based catalyst is [NH$_2$Me$_2$][{RuCl((S)-SegPhos)}$_2$(μ-Cl)$_3$] or [NH$_2$Me$_2$][{RuCl((R)-DM-SegPhos)}$_2$(μ-Cl)$_3$].

In some embodiments, the ketone group in the compound of Formula (A) is reduced using Ru(OAc)$_2$((R)-SegPhos) and methanol.

In some embodiments, the method described herein includes reducing the ketone group in the compound of Formula (A) with an alcohol dehydrogenase system.

In some embodiments, the alcohol dehydrogenase system comprises a reduced nicotinamide adenine dinucleotide (NADH), a reduced nicotinamide adenine dinucleotide phosphate (NADPH), and an alcohol.

In some embodiments, the alcohol is isopropyl alcohol.

In some embodiments, the reduction is performed at a pH less than about 8. In some embodiments, the reduction is performed at a pH less than about 7.5. In some embodiments, the reduction is performed at a pH less than about 7. In some embodiments, the reduction is performed at a pH in the range of about 5 to 8, about 5.5 to 7.5, about 6 to 6.5. In some embodiments, the reduction is performed at pH about 6.

In some embodiments, the method described herein includes dividing and adding reaction reagents in two or more portions. In some embodiments, the method described herein includes dividing and adding the compound of Formula (A) into two or more portions.

In some embodiments, the method described herein includes applying vacuum prior to adding a new portion of reaction reagents. In some embodiments, the method described herein includes applying vacuum prior to adding a new portion of the compound of Formula (A).

In some embodiments, the resulted compound (B) has an enantiomeric excess of more than 80%. In some embodiments, the resulted compound (B) has an enantiomeric excess of more than 90%. In some embodiments, the resulted compound (B) has an enantiomeric excess of more than 92%, 94%, 95%, 96%, 97%, 98%, or 99%.

In some embodiments, R$^2$, R$^{4a}$ and R$^{4b}$ are each independently a butyl group. In some embodiments, R$^2$ is a t-butyl group and R$^{4a}$ and R$^{4b}$ n-butyl group. In some embodiments, R$^2$, R$^{4a}$ and R$^{4b}$ are each independently optionally substituted C$_{1-6}$ alkyl group.

Some embodiments relate to a method of making the compound of Formula (C) by adding a boronate to the compound of Formula (B-1).

Some embodiments relate to a compound of making the compound of formula (D) from the compound of Formula (C) using a Grignard reagent. In some embodiments, the Grignard reagent is magnesium.

In some embodiments, R$^2$, R$^{4a}$ and R$^{4b}$ are independently a butyl group. In some embodiments, R$^2$ is a t-butyl group, and R$^{4a}$ and R$^{4b}$ are n-butyl group.

In some embodiments, the compound of Formula (D) is

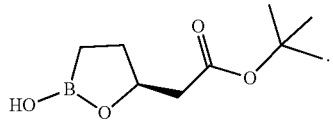

In some embodiments, the method described herein further includes mixing ZnCl$_2$ with magnesium to react with the compound of Formula (C).

In some embodiments, the method described herein further includes adding acid to hydrolyze the first reaction intermediate.

In some embodiments, the method described herein further includes adding dichloromethane to the reaction mixture after the hydrolysis of the first reaction intermediate.

Some embodiments relate to a method of making the compound of Formula (E) by reacting the compound of Formula (D) with the complexing agent of Formula (CL).

In some embodiments, for the compound of Formula (D) and (E), $R^2$ is a butyl group. In some embodiments, $R^2$ is a t-butyl group.

In some embodiments, for the compound of Formula (D) and (E), m is 2. In some embodiments, for the compound of Formula (CL) and (E), n is 2.

In some embodiments, the compound of Formula (E) is

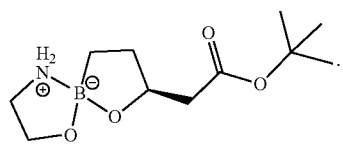

In some embodiments, the complexing agent of Formula (CL) is $NH_2(CH_2)_2OH$.

In some embodiments, the compound of Formula (E) has the structure of Formula (E-1):

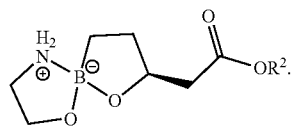

In some embodiments, the method described herein further includes reacting the compound of Formula (E) with pinanediol to form a compound of Formula (F)

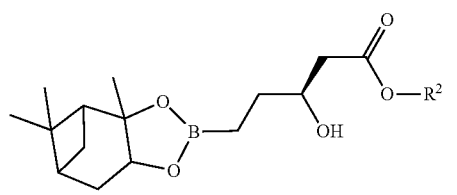

(F)

protecting the hydroxy group of the compound of Formula (F) with a PG group to form a compound of Formula (G),

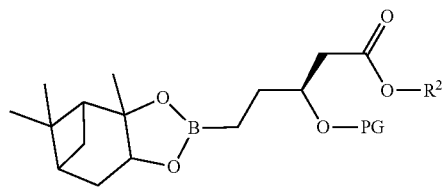

(G)

reacting the compound of Formula (G) with n-butyl-lithium and dichloromethane to form a compound of Formula (H), and

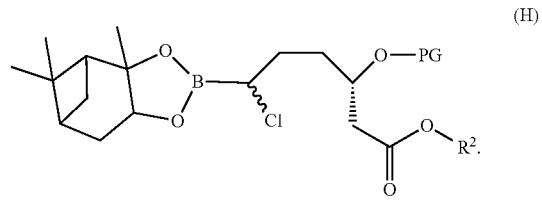

(H)

reacting the compound of Formula (H) with an LiN[Si$(R^{12})_3]_2$ to form a compound of Formula (J)

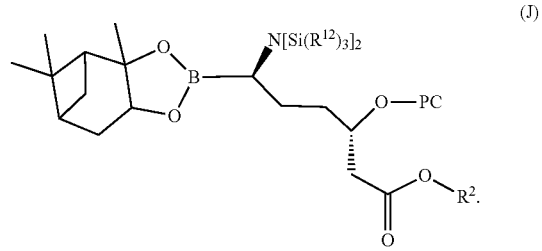

(J)

reacting the compound of Formula (J) with $R^{13}$—COCl to form a compound of Formula (K)

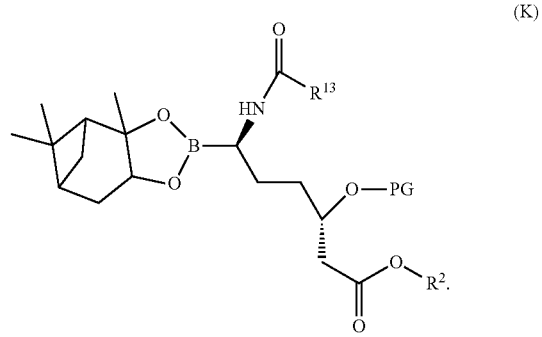

(K)

removing the PG group on the compound of formula (K) to form a compound of formula (L):

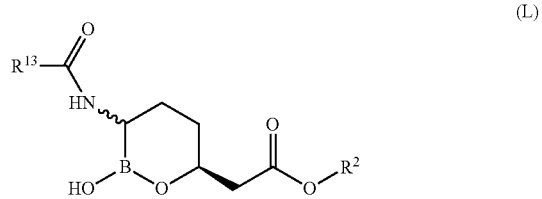

(L)

wherein:

PG is a hydroxy protection group, $R^{12}$ is optionally substituted phenyl or optionally substituted $C_{1-8}$ alkyl, and $R^{13}$ is selected from optionally substituted $C_{1-8}$ alkyl, optionally substituted $C_{0-4}$ alkyl-$C_{6-10}$ aryl, optionally substituted $C_{0-4}$ alkyl-5-10 membered heteroaryl, optionally substituted $C_{0-4}$ alkyl-$C_{3-10}$ carbocyclyl, and $C_{0-4}$ alkyl-4-10 membered heterocyclyl.

In some embodiments, the compound of Formula (G) reacts with the n-butyllithium and dichloromethane at a temperature lower than −90° C. to form the compound of Formula (H).

In some embodiments, the PG group is a tert-Butyldimethylsilyl group.

In some embodiments, $R^2$ is t-butyl group.

In some embodiments, $R^{13}$ is

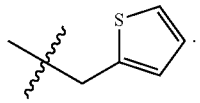 [SMILES: *Cc1cccs1]

In some embodiments, the compound of Formula (L) is

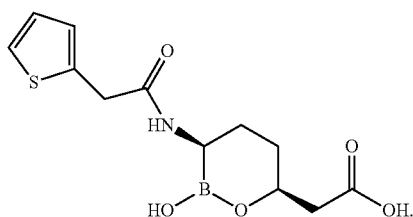 [SMILES: O=C(O)C[C@@H]1CC[C@H](NC(=O)Cc2cccs2)B(O)O1]

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims. Unless otherwise indicated, substituent variables in the following schemes have the same definitions as elsewhere in this application.

An exemplary but non-limiting general synthetic scheme for preparing the intermediate compound of Formula

EXAMPLES

Example 1—Stability of Compound 1

The stability of Compound 1 was studied and it was found that the keto ester of Compound 1 is very unstable in aqueous environment. Upon incubation in phosphate buffer (pH=7.5) for 24 hours at 28° C. less than 10% of the original amount of Compound 1 remained. At the same time a significant increase of the degradation product was observed.

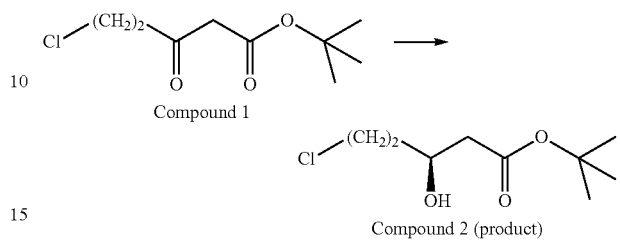

The stability of Compound 1 was also tested with the bioreduction enzyme system. This test was performed by incubation of 40 mM compound 1 at 28° C. in phosphate buffer and co-factors/co-factor regeneration system (NADH, NADPH, glucose/GDH solution) at pH 6.5 and 7.5. The test results showed that Compound 1 was more stable at lower pH. However, decomposition still occurred relatively fast at pH 6.5.

Example 2—Bioreduction of Compound 1 at Different pH

The reduction of Compound 1 was tested using an alcohol dehydrogenase bioreduction system. This experiment was performed on 250 μL scale using compound 1 at a concentration of 40 mM (about 1% w.t.). The bioreduction reaction was tested at pH 7.5 and pH 6.5.

When the reaction was performed at pH 6.5, approximately 85% conversion was achieved within 2 hours. At pH 7.5 the performance of the enzyme was not as good as at pH 6.5, i.e. significantly lower levels of conversion were achieved. FIG. 1 shows the reaction comparison of pH 6.5 and pH 7.5, and the conversion rate was calculated based on the remaining amount of Compound 2 (product).

A sample from the experiment at pH 7.5 was freeze dried. Compound 2 (product) was analyzed by chiral GC after being converted to a corresponding trifluoroacetate. Based on this analysis the enantiomeric excess of Compound was determined to be at least 99%.

Example 3—Bioreduction of Compound 1 with Different Co-Factor Regeneration System Two different co-factor regeneration systems were tested, i.e. the original GDH/glucose system as well as 2-propanol (IPA). The experiments were performed on 2 mL scale at pH=6.5. The experimental data showed that the GDH/glucose based system had difficulties in producing more than 50-60 mM of Compound 2. The reaction progress with the GDH/glucose system is shown in FIG. 2. The reaction was fast but leveled off after approximately 4 hours. This may be related to a pH effect, i.e. the co-factor regeneration results in the formation of gluconic acid which may reduce the pH to a level where the enzyme becomes deactivated. The data also reflected the limited stability of the substrate, i.e. the decrease of Compound 1 on average was higher than the amount of Compound 2 that was being formed.

The performance of the IPA-system was better, i.e. higher concentrations of Compound 2 could be achieved. The reaction progress of the IPA system is shown in FIG. 3. In this case the reaction more or less stopped after 4 hours. The incomplete conversion of Compound 1 might by due to the presence of acetone, which was generated during the co-factor regeneration.

Example 4. Effect of Acetone on Bioredcution Reaction

The effect of acetone on the reduction was tested and the result is shown in FIG. 4. Experiments were performed with 200 mM of Compound 1 as starting materials, and one experiment had additional acetone added while the other experiment did not. When additional acetone was added to the reaction mixture, only 80 mM of Compound 2 was obtained as compared to 120 mM in the absence of additional acetone. The bioreduction of Compound 1 was hampered by the acetone that was generated during the co-factor regeneration process.

Two experiments were performed in parallel using 200 mM of Compound 1. The first experiment was performed without any vacuum applied whereas in the second experiment vacuum was applied (2 minutes 100 mbar every 20 minutes during the first 4 hours of the reaction). The reactions were sampled, and the concentration of Compound 2 formed and the remaining amount of Compound 1 were determined by HPLC analysis. The conversion curves based on this data are shown in FIG. 5. As shown in FIG. 5, the removal of acetone increased the conversion rate of this bioreduction reaction.

Example 5—Bioreduction of Compound 1 Preparation Scale

The reduction of Compound 1 was performed in a pH-stat equipment using an alcohol dehydrogenase system. The starting reagents included 1 mM NADH, 1 mM NADPH, 20% v/v IPA, 20% v/v CFE, Buffer, and 0.1 mM KPi pH 6.5, and the final volume of the starting reagents was 40 ml. The starting materials were stirrer speed at a reaction temperature of 28° C. Before adding compound 1 to start the reaction, the pH was set to 6.0 using HCl. During the reaction the pH was maintained constant by titration with 1M NaOH.

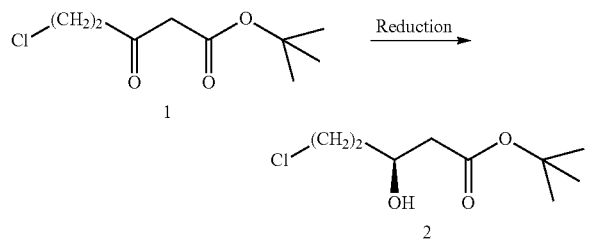

Reaction was started by adding 200 μL of compound 1. A new portion of 200 μL Compound 1 was added every 20 min with a total dosing time of 200 min and a total dosing amount of 2.1 g. Before adding each new portion of Compound 1, vacuum (about 160 mbar) was applied for 1 min to remove the acetone in the reaction mixture. After the total amount of Compound 1 was added, vacuum was applied 3 times with a 20 min interval. Subsequently, vacuum was applied once per hour for another 4 hours.

After an overnight incubation, the reduction product was isolated by extraction with methyl tert-butyl ether (MTBE).

First, the reaction mixture was mixed with about 100 ml MTBE; and about 4 g Dicalite were then added to mixture. Filtration was performed using a glass filter coated with Dicalite. The filtrate was phase-separated and both phases (water and organic phase) as well as the filter cake were analyzed. The water and organic phase were analyzed after being diluted 1:5 with acetonitrile. The filter cake was mixed with acetonitrile, centrifuged and the supernatant was analyzed, and the results are shown in Table 1. Test A was performed without taking any samples, while Test B was performed with samples taking every 20 min. The enantiomeric excess of the isolated alcohol was more than 99%.

TABLE 1

| Bioreduction of Compound 1 to form Compound 2 obtained in two tests | | |
|---|---|---|
| | Test A | Test B |
| Yield (product/starting substrate) | 88.87 | 82.20 |
| remaining substrate [%] | 2.55 | 2.17 |
| Product loss in filter cake [%] | 0.78 | 0.85 |
| Mass balance | 92.2 | 86.23 |

*based on detection limit of 0.1 mg/ml

Example 6—Asymmetric Hydrogenation Solvent Screening

The asymmetric hydrogenation was performed at ambient temperature with 25 bar $H_2$ in a selection of solvents including methanol, ethanol, IPA, ethyl acetate, DCM, $C_6H_5Cl$, DMF, and THF. The best performance was achieved in methanol, in which case a high conversion to the desired Compound 2 was achieved. The enantiomeric excess of the obtained product was found to be 88%. In ethanol the reaction was more sluggish and no full conversion was achieved. In addition, the enantiomeric excess of Compound 2 was somewhat lower (82%). In the other solvents (virtually) no conversion of Compound 1 could be achieved.

Example 7—Asymmetric Hydrogenation Catalyst Screening

The asymmetric hydrogenation reactions were performed with 2.8 mmol (720 mg with an assay of 80% w.t.) Compound 1 in 4.2 ml of solvent at 5 bar $H_2$ and 25° C. in a selection of catalysts including A:Ru(OAc)$_2$((R)-BINAP); B: Ru(OAc)$_2$((R)-SegPhos), C: Ru(OAc)$_2$((R)-SegPhos), D: Ru(OAc)$_2$((R)-DM-SegPhos); E: [NH$_2$Me$_2$][{RuCl((S)-SegPhos®)}$_2$μ-Cl)$_3$]; F: [NH$_2$Me$_2$][{RuCl((R)-DM-SegPhos®)}$_2$μ-Cl)$_3$]. The reaction results are shown in Table 2.

TABLE 2

| Catalyst screening results | | | | | |
|---|---|---|---|---|---|
| Catalyst | catalyst loading | Solvent | time (h) | Assay yield (%) | e.e (%) |
| A | 0.5 | MeOH | 4 | 91 | 95 |
| B | 0.5 | | 4 | 40 | 94 |
| C | 0.5 | MeOH | 4 | 45 | 93 |
| D | 0.5 | MeOH | 4 | 10 | 88 |
| A | 0.5 | IPA | 17 | 1 | — |
| C | 0.5 | IPA | 17 | — | — |
| D | 0.5 | MeOH | 17 | 68 | 85 |
| D | 0.5 | IPA | 17 | 2 | 78 |
| E | 0.25 | MeOH | 17 | 88 | 85 |
| F | 0.25 | MeOH | 17 | 96 | 75 |

TABLE 2-continued

Catalyst screening results

| Catalyst | catalyst loading | Solvent | time (h) | Assay yield (%) | e.e (%) |
|---|---|---|---|---|---|
| E | 0.25 | IPA | 17 | — | — |
| F | 0.25 | IPA | 17 | 3 | 78 |
| A[a] | 0.5 | MeOH | 17 | 86 | 69 |
| A[b] | 0.5 | MeOH | 17 | 84 | 70 |
| A[a] | 0.5 | IPA | 17 | — | — |
| A[b] | 0.5 | IPA | 17 | — | — |

[a]In the presence of 6 mol % HCl;
[b]in the presence of 6 mol % HCl and 1% LiCl As shown in Table 2, Ru(OAc)$_2$((R)-BINAP) showed the best performance in the asymmetric hydrogenation of Compound 1. That is remarkable as Noyori reported BINAP-Rucarboxylate complexes to be completely ineffective in the hydrogenation of β-keto esters (JACS 1987, 109, 5856). The corresponding halogen complexes were found to be much more active.

It was therefore speculated that the actual catalytic species in the asymmetric hydrogenation of Compound 1 is not the carboxylate complex, but rather the chloride complex which may be formed in situ from Ru(OAc)$_2$((R)-BINAP) and HCl (released from Compound 1). Alternatively, the HCl may promote enolisation of Compound 1 in which case the reduction of Compound 1 actually occurs via hydrogenation of the enol (C=C hydrogenation) and not the ketone (C=O hydrogenation). This would match with the fact that Ru(OAc)$_2$((R)-BINAP) is known to be a suitable catalyst for the hydrogenation of olefins.

In addition to the catalyst listed in Table 2, 10 additional catalysts RuBr$_2$(Ligand) were synthesized and tested in the hydrogenation of compound 1 in methanol at 25° C. and 5 bar H$_2$. The results are shown in Table 3.

TABLE 3

Catalyst screening results

| Ligand | e.e. (%) |
|---|---|
| (R)-tolyl-BINAP | 83 |
| (R)-xylyl-BINAP | 74 |
| (S)-tolyl-BINAP | 81 |
| (S)-BINAPHANE | no conversion |
| (S)-PhanePhos | 61 |
| JosiPhos-2-1 | 80 |
| (R)-SolPhos SL-A001-1 | 83 |
| (S)-MeOBiPhep | 77 |
| (S)-P-Phos | 92 |
| (S)-(+)-DTBM-SEGPHOS ® | 62 |

As shown in Table 3, BINAP and SegPhos® type of ligands (table 6) are the most selective ligands in the hydrogenation of Compound 1.

More Ru-based catalysts were tested in a range of solvents, and the results were shown in Table 4. The base (triethylamine) was added into one reaction mixture as a additive.

TABLE 4

Catalyst screening results in different solvents

| Catalyst | Solvent | H$_2$ (bar) | Additive | yield (%) | e.e (%) |
|---|---|---|---|---|---|
| [RuCl$_2$(benzene)]$_2$/(S)-BINAP in DMF | DMF/MeOH (1.5:1) | 5 | none | 2 | 97 |
| [RuCl$_2$(benzene)]$_2$/(S)-BINAP in DMF | DMF/MeOH (1.5:1) | 5 | none | 14 | 97 |
| [RuCl$_2$(cymene)]$_2$/(S)-BINAP in DMF | DMF/MeOH (1.5:1) | 5 | none | 2 | 76 |
| RuBr$_2$((S)-BINAP) | AcOH | 5 | none | — | — |
| Ru(OAc)$_2$((R)-H$_8$-BINAP) | MeOH | 5 | none | 91 | 91 |
| Ru(OAc)$_2$((R)-SegPhos) | MeOH | 5 | none | 91 | 93 |
| Ru(OAc)$_2$((R)-DM-SegPhos) | MeOH | 5 | none | 68 | 84 |
| [NH$_2$Me$_2$][{RuCl((S)-SegPhos ®)}$_2$(μ-Cl)$_3$] | AcOH | 5 | none | — | — |
| ([RuCl$_2$(benzene)]$_2$/(R)-BINAP)dmf | MeOH | 5 | none | 96 | 88 |
| ([RuCl$_2$(cymene)]$_2$/(R)-BINAP)dmf | MeOH | 5 | none | 94 | 88 |
| RuCl$_2$((S)-BINAP) in DMF | DMF/MeOH (1.4:1) | 5 | none | 226 | — |
| RuCl$_2$((S)-BINAP) in DMF | DMF/MeOH (1.4:1) | 25 | none | 26 | 96 |
| RuCl$_2$((R)-BINAP) | MeOH | 5 | none | 92 | 87 |
| RuCl$_2$((R)-BINAP) | MeOH | 5 | Et$_3$N | 91 | 98 |
| RuCl$_2$((R)-BINAP) | MeOH | 5 | none | 92 | 87 |
| RuCl$_2$((R)-BINAP) | TFE | 5 | none | 2 | — |
| RuCl$_2$((S)-BINAP) in DMF | MeOH | 5 | none | 91 | 87 |
| RuCl$_2$((S)-BINAP) in DMF | MeOH | 5 | none | 1 | — |
| RuCl$_2$((R)-BINAP) | DCM/MeOH (1:3) | 5 | none | 94 | 87 |
| RuCl$_2$((R)-BINAP) | DCM/MeOH (1:1) | 5 | none | 94 | 82 |

As shown in able 4, the results clearly show that the presence of triethylamine significantly improved the enantioselectivity of the Ru(BINAP)Cl$_2$ catalyzed hydrogenation of Compound 2 (98% e.e. as compared to 87% in the absence of base).

Example 8—Asymmetric Hydrogenation Catalyst Screening Additive Effect

More catalysts were tested in the presence of trimethylamine. The results are shown in Table 5.

TABLE 5

Catalyst screening results in the presence of Et$_3$N

| Catalyst | Solvent | Additive[1] | Time (h) | yield (%) | e.e (%) |
|---|---|---|---|---|---|
| RuBr$_2$((S)-BINAP) | MeOH | | 8 | 92 | 97.0 |
| [NH$_2$Me$_2$][{RuCl((S)-SegPhos ®)}$_2$(µ-Cl)$_3$] | MeOH | | 16 | 94 | 93.3 |
| RuCl$_2$((R)-BINAP) | DMF/MeOH (2.5:1.7) | | 16 | 3 | 97.5 |
| RuCl$_2$((S)-BINAP)dmf | DMF/MeOH (2.5:1.7) | | 16 | 2 | 97.4 |
| RuCl$_2$((R)-BINAP) | MeOH | LiCl | 2 | 95 | 96.5 |
| RuCl$_2$((R)-BINAP) | MeOH | ZnCl$_2$ | 3 | 91 | 86.7 |
| RuCl$_2$((R)-BINAP)[a] | MeOH | ZnCl$_2$ | 2 | 94 | 96.6 |
| [NH$_2$Me$_2$][{RuCl((S)-SegPhos ®)}$_2$(µ-Cl)$_3$] | MeOH | | 18 | 26 | 98.2 |
| Ru(OAc)$_2$( ®-BINAP) | MeOH | | 1.5 | 94 | 98.4 |
| Ru(Oac)$_2$( ®-BINAP) | MeOH | LiCl | 1.5 | 94 | 98.3 |
| RuCl$_2$((R)-BINAP) | MeOH (5% v.v H$_2$O) | | 7 | 137 | 91.6 |
| Ru(OAc)$_2$((R)-BINAP) | MeOH | | 1.5 | 96 | 98.3 |
| Ru(OAc)$_2$((R)-BINAP) | MeOH/EtOH (1:1) | | 2 | 95 | 98.3 |
| Ru(OAc)$_2$((R)-BINAP) | MeOH/IPA (1:1) | | 4.5 | 72 | 98.0 |
| Ru(OAc)$_2$((R)-DM-SegPhos) | MeOH | | 18 | 96 | 98.6 |
| Ru(OAc)$_2$((R)-SegPhos) | MeOH | | 6.5 | 96 | 99.5 |
| Ru(OAc)$_2$((R)-H8-BINAP) | MeOH | | 4 | 97 | 98.9 |
| Ru(OAc)$_2$((R)-T-BINAP) | MeOH | | 2 | 97 | 97.7 |
| Ru(OAc)$_2$((R)-DM-BINAP) | MeOH | | 5 | 1 | 98.2 |
| RuCl$_2$((S)-BINAP) | MeOH | | 20 | 32 | — |
| Ru(OAc)$_2$((R)-BINAP) | EtOH/IPA 1:1 | | 20 | 96 | 96.4 |
| Ru(OAc)$_2$((R)-BINAP) | MeOH/IPA 1:1 | | 5 | | 97.7 |

[1] 2 equiv. Relative to Ru;
[2] Reaction time to full conversion or maximum run time according to the hydrogen uptake curves.
[3] Internal standard not completely dissolved; full conversion.
[a] no Et3N was added.

The results listed in Table 5 show that the positive effect exhibited by triethylamine is not limited to the BINAP-based catalysts. The selectivity of the hydrogenation reaction was also improved in the presence of this base in the SegPhos®-ligand family. Application of Ru(OAc)$_2$((R)-SegPhos) in combination with triethylamine provided Compound 2 in 96% yield and 99.5% enantiomeric excess. With the antipode of the same catalyst (S/C=200) the desired product 1 was obtained in 93% yield and 99.3% enantiomeric excess.

Asymmetric hydrogenation at lower catalyst loading (S/C=500) resulted in complete conversion within 15 hours and a marginally lower selectivity (99% ee). At S/C=1000 the reaction was still not complete after 20 hours and the selectivity dropped to 98% ee. This suggests that application of a low catalyst loading may require purification of Compound 1.

When the optically pure Compound 2 was used to make Compound 3, Compound 4, and Compound 5, no erosion of enantiomeric excess occurred during the later steps. Therefore, asymmetric hydrogenation of Compound 1 using Ru(OAc)$_2$((R)-SegPhos) as the catalyst provided the desired hydroxy ester Compound 2 in excellent yield and enantiomeric excess.

Example 9—Asymmetric Hydrogenation of Compound 1

The asymmetric hydrogenation was conducted with crude Compound 1 having a purity of 80% ($^1$H NMR). Crude Compound 1 (0.72 g, 2.8 mmol) was placed in a 5 mL vial and hexadecane (48 µL) was added as the internal standard. In order to remove HCl the vial was placed under vacuum for 0.25 hours. The mixture of Compound 1 and internal standard was dissolved in methanol (4.2 mL), and 10 µL of triethylamine was later added to form a starting material.

Ru(OAc)$_2$((S)-SegPhos) (11.6 mg; S/C=200) was placed in an Endeavor glass tube and subsequently the starting material was added. The glass tube was placed in the Endeavor parallel reactor and the reactor was closed under a flow of nitrogen gas followed by inertisation with 5 cycles of N$_2$ (3 bar). The nitrogen head space was replaced by hydrogen by 5 cycles of H$_2$ (25 bar). The hydrogenations were carried out using 5 bar of H$_2$ pressure at 25° C.

IPC: A sample (50 µL) was dissolved in DCM (1 mL). The solution was analyzed by GC equipped with a HP 5 column. Oven: 80° C. 3 min., 10° C./min→300° C., 300° C. 5 min.

Enantiomeric excess: A sample (10 µL) was placed in a 1.5 mL vial and the solvent was removed by placing the sample in a vacuum oven at ambient temperature. The residue was dissolved in trifluoroacetic anhydride (TFAA) (100 µL) and the mixture diluted with DCM (1 mL). The solution was analyzed by chiral GC.

Work-up: The reaction mixtures of several of these reactions were pooled in a 250 mL Schlenk vessel. In order to avoid transesterification, the methanol was subsequently removed in vacuo at 20° C. and the methanol was collected in a cold-trap filled with liquid nitrogen. The residue was subjected to distillation at <0.2 mbar starting at an oil bath temperature of 90° C. which was slowly increased to 120° C. providing 5.52 g colorless liquid. The purity of the reduced product was about 92.4 w %, the isolated yield corrected for its purity was 87%, and the e.e. was 99.3%.

Example 10—Intramolecular Grignard Reaction

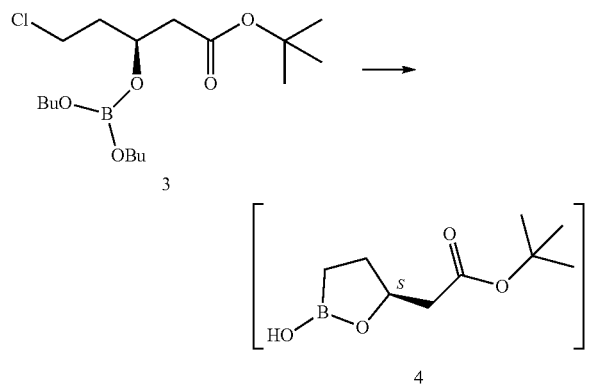

When making alkylboronate compound 4 from Compound 3, the zinc-insertion method resulted in the des-chloro compound after aqueous work-up. Magnesium insertion resulted in one major product (73 area % by means of GC-analysis). Addition of additives were tested in the Grignard reaction. When LiCl and MgCl₂ were tested, their use resulted in significant levels of deschlorination and side products. However, in the presence of two equivalents of ZnCl₂ a clean conversion to Compound 4 was achieved.

To test the effect of the additive, a 1.5 mL vial was placed in the glove box, the additive and clear DMF Zn-adduct solution (0.1 mL) and the mixture was allowed to stir for 15 minutes at 80° C. (in case the additive was a solvent, pre-treatment at 80° C. was not performed). The mixture was cooled to ambient temperature after which the (Pin)BOMe (33 μL, 0.2 mmol) was added. After addition of the borate ester the mixture was heated overnight at elevated temperature. The complete reaction mixture was treated with water (0.5 mL) and subsequently extracted with DCM (1 mL). Part of organic phase (0.5 mL) was, diluted with DCM (0.5 mL) and dried over Na₂SO₄. The DCM-was analyzed by GC. Any remaining the Zn-adduct was detected as deschloro compound 6.

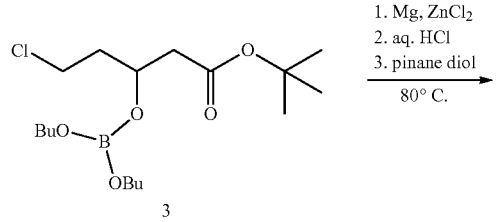

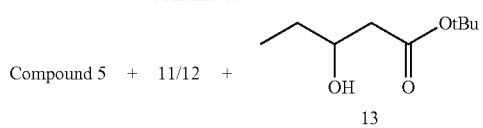

The effect of the ZnCl₂ was tested at different equivalence of the starting material Compound 3, and the results are shown in Table 6.

TABLE 6

Effect of ZnCl₂ on the Grignard reaction

| ZnCl₂ [equiv] | t [h] | 13 [area %] | 11/12 [area %] | Compound 4 [area %] |
|---|---|---|---|---|
| 1[a] | 1.5 | 12 | <1 | 75 |
| 1 | 1.5 | 12 | <1 | 76 |
| 0.5 | 1.5 | 20 | <1 | 70 |
| 0.1 | 1.5 | 32 | 18 | 29 |
| 1[a,b] | 2 | 5 | <1 | 86 |

All experiments at 0.05-0.1 mol scale, substrate concentration 0.1M unless indicated otherwise.
[a]experiment at 0.2M Compound 3.
[b]experiment at 0.5 mol scale The effect of ZnCl₂ as an additive was further tested at several equivalence ratios with different amount of magnesium used for the reaction, and the results are collected in table 7.

TABLE 7

Effect of ZnCl₂ on the Grignard reaction

| Mg [equiv] | ZnCl₂ [equiv] | T [° C.] | t [h] | Compound 4 [%] | 13 [area %] |
|---|---|---|---|---|---|
| 1.6 | 0.5 | 80 | 1.25 | 54 | 3.9 |
| 1.6 | 0.5 | 25 | 40 | 65 | 3.8 |
| 1.6 | 0.5 | 25 | 19 | 63 | 4.2 |
|  |  | 40 | +2 | 64 | 4.7 |
|  |  | 60 | +2 | 69 | 3.9 |
|  |  | 80 | +1 | 45 | 5.4 |
|  |  | 80 | +17 | 1 | — |
| 1.6 | 1.0 | 25 | 21 | 37 | — |
| 3.2 | 0.5 | 25 | 22 | 82 | — |

As shown in Table 7, the reaction proceeded smoothly at ambient temperature using unactivated magnesium dust. In fact, at elevated temperature the yield of the reaction dropped. An excess of magnesium was required to achieve full conversion of the substrate. In one reaction, Compound 4 was obtained in approximately 80% yield (based on GC-analysis of Compound 5; experiment at 0.5 mmol scale and 0.5M substrate concentration.

Example 11—Synthesis of Compound 5
Preparative Scale

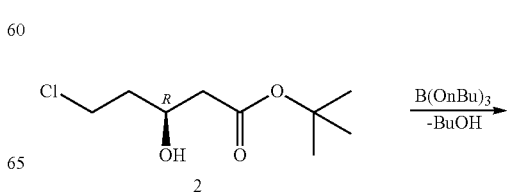

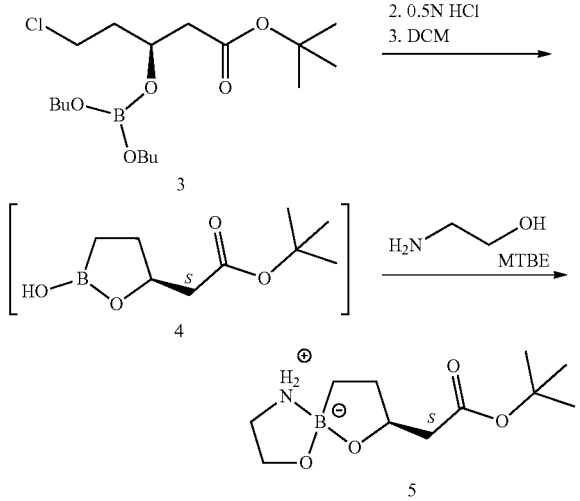

To a flame dried Schlenk flask containing B(O-nBu)₃ (Fw 230.15, 6.10 g, 26.5 mmol) was added the optically enriched hydroxy ester Compound 2 (5.25 g; assay 92%; e.e. 99.3%, 23.1 mmol). The mixture was allowed to stir under high vacuum (<0.2 mbar) for 2 hours at ambient temperature, while trapping the evaporated n-butanol in liquid nitrogen.

The residue was dissolved in dry THF (40 mL), and subsequently Mg (Fw 24.3, 2.13 g, 88 mmol) and ZnCl₂ (Fw 136.30, 1.81 g, 13.3 mmol) was added. The mixture was stirred at 24° C. for 24 hours (GC-analysis showed complete conversion of the starting material).

The mixture was cooled to 5° C. with an ice bath and subsequently quenched with 1 N HCl (150 mL). Residual magnesium was removed by filtration. Subsequently the filtrate was extracted with MTBE (80 mL). After phase separation the water layer was extracted with MTBE (2×33 mL). The combined organic phase was concentrated in vacuo at 60° C. Residual amounts of 1-butanol were removed by a stream of N₂ providing 5.82 g of crude Compound 4.

For complexation with ethanolamine (Fw 61.08, d 1.012), the residue was dissolved in CH₃CN (3.2 mL). Subsequently ethanolamine (1.52 g; 25 mmol) was added. Slow addition of MTBE (19 mL) resulted in the precipitation of solid material accompanied by some oily material. The mixture was stirred overnight and subsequently diluted with heptane (19 mL). The precipitated Compound 5 was isolated by filtration as a white solid (2.73 g; 11.2 mmol; 49% yield; ee 99.5%).

Example 12—Synthesis of Rac-Compound 5 (Intramolecular Approach, 0.8 g Scale)

To a flame dried Schlenk flask containing B(O-nBu)₃ (Fw 230.15, 905 mg, 3.93 mmol) was added hydroxy ester Compound 2 (assay 96%, 780 mg, 3.59 mmol). The mixture was allowed to stir under high vacuum (0.05 mbar) for 45 minutes hour at ambient temperature, while trapping the evaporated n-butanol in liquid nitrogen.

In a second flame dried flask magnesium (298 mg; 12.3 mmol) and ZnCl₂ (254 mg; 1.869 mmol) was stirred in 7.5 ml of dry THF. Subsequently, the content of the first flask was transferred to the second flask and obtained reaction mixture was stirred for 20 hours at ambient temperature. According to GC-analysis this mixture still contained a small amount (2 area %) of Compound 2.

The reaction mixture was transferred to a 100 mL conical flask, cooled to 0° C. and subsequently 15 mL of 1 N aqueous HCl was slowly added. Stirring was continued while the mixture was allowed to warm up to ambient temperature. This mixture was extracted with DCM (3×50 ml), the combined organic phases were dried over Na₂SO₄ and subsequently concentrated in vacuo. Residual amounts of DCM were removed by a stream of N₂. 0.73 g of Compound 4 was made. A sample of the crude Compound 4 (2.24 mg) was dissolved in DCM (1 mL). Subsequently hexadecane (2.03 mg) and pinanediol (8.59 mg) were added and the solution was analyzed by GC. Based on the analysis of the pinanediol boronate adduct of the product, the assay of the crude Compound 4 was determined to be 81 w %, which corresponds with a yield of 82%.

The crude Compound 4 was dissolved in dry 1,4-dioxane (3.6 ml) and subsequently ethanolamine (d:1.012, Fw: 61.08, 220 mg, 3.6 mmol) was added. In order to speed up the precipitation of Compound 5 the mixture was seeded with Compound 5 (2 mg). After 2.5 hours of stirring, Compound 5 started to precipitate. Heptane (1.8 mL) was added and the mixture was allowed to stir overnight. As a result the mixture turned into a gel-like substance which was no longer stirrable.

Filtration of the Compound 5 was therefore difficult. The mixture was diluted with a couple of mL of heptane and transferred to a filter. The mixture was filtered and washed with 1,4-dioxane (2×2.5 mL). Washing was not easy, since the material was sticky. After drying in air giving Compound 5 was obtained as an off white solid (416 mg, 1.71 mmol, 48% yield). ¹H-NMR spectrum is in agreement with reference sample. The overall yield is uncorrected for losses due to sampling and technical losses.

Example 13. Synthesis of Rac-Compound 5 (Intramolecular Approach, 2.1 g Scale)

To a flame dried Schlenk flask containing B(OnBu)₃ (Fw 230.15, 2.42 g, 10.5 mmol) was added the hydroxy ester Compound 2 (2.10 g, 10 mmol). The mixture was allowed to stir under high vacuum (0.05 mbar) for 75 minutes hour at ambient temperature, while trapping the evaporated n-butanol in liquid nitrogen.

The residue was dissolved in dry THF (20 mL) and subsequently Mg (Fw 24.3, 802 mg, 33 mmol) and ZnCl₂ (Fw 136.30, 682 mg, 5 mmol) was added. The mixture was stirred at 24° C. for 27 hours (GC-analysis showed complete conversion of the starting material).

The reaction mixture was transferred to a 300 mL conical flask. Residual amounts of reaction mixture were transferred by rinsing with THF. The mixture was cooled to 5° C. with an ice bath and subsequently quenched with 1 N HCl (60 mL). The Mg did not dissolve completely. Subsequently the mixture was extracted with MTBE (32 mL). After phase separation the water layer was extracted with MTBE (2×13 mL). The combined organic phase was concentrated in vacuo at 60° C. Residual amounts of 1-butanol were removed by a stream of N₂ providing 2.05 g of crude Compound 4.

For complexation with ethanolamine (Fw 61.08, d 1.012), the residue was dissolved in CH₃CN (1.3 mL) and MTBE (7.5 mL) followed by the addition of ethanolamine (610 mg, 10 mmol). The addition of ethanolamine was accompanied by immediate precipitation of an off white solid. The mixture was allowed to stir over the weekend. Compound 5 was filtered off, washed with MTBE (7.5 mL) and dried giving Compound 5 in 1450 mg (6.0 mmol, 60%) isolated yield.

What is claimed is:
1. A compound having the structure of Formula (I):

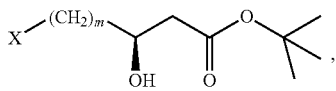

wherein X is a halogen and m is 2, 4, 5, or 6.
2. The compound of claim 1, wherein X is Cl and m is 2.
3. A compound having the structure of Formula (II):

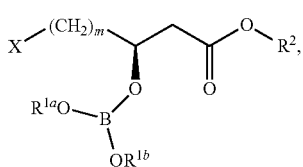

or a salt thereof, wherein:
X is a halogen;
m is an integer between 2 and 6;
each of $R^{1a}$ and $R^{1b}$ is independently selected from the group consisting of an optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl, and optionally substituted heteroaryl, or
$R^{1a}$ and $R^{1b}$ together with intervening atoms optionally form a 5-7 membered boron ester ring; and
$R^2$ is selected from the group consisting of an optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl, and optionally substituted heteroaryl.
4. The compound of claim 3, wherein X is Cl and each of $R^{1a}$ and $R^{1b}$ is a butyl group.
5. A method of making a compound of Formula (B), comprising the steps of:
reducing the ketone group of a compound of Formula (A):

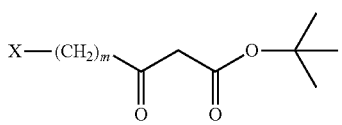

to form a compound of Formula (B):

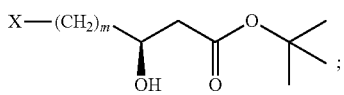

wherein:
X is Cl;
m is 2;
the ketone group in the compound of Formula (A) is reduced using Ru(OAc)$_2$((R)-SegPhos) and methanol; and
the compound of Formula (B) is produced in an enantiomeric excess of greater than 99%.
6. A method of making a compound of Formula (B), comprising the steps of:
reducing the ketone group of a compound of Formula (A):

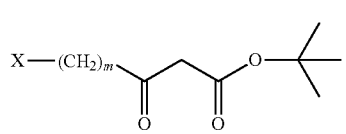

to form a compound of Formula (B):

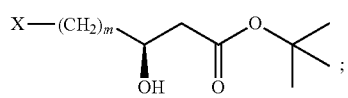

wherein:
X is Cl;
m is 2; and
the ketone group in the compound of Formula (A) is reduced with an alcohol dehydrogenase system, wherein
the alcohol dehydrogenase system comprises a reduced nicotinamide adenine dinucleotide (NADH), a reduced nicotinamide adenine dinucleotide phosphate (NADPH), and an alcohol,
the alcohol is isopropyl alcohol,
acetone is generated as a by-product,
the acetone is removed under vacuum, and
the compound of Formula (B) is produced in an enantiomeric excess of greater than 99%.
7. A method of making a compound of Formula (C), comprising:
reacting a boronate compound B(OR$^{4a}$)(OR$^{4b}$)(OR$^{4c}$) with a compound of Formula (B-1):

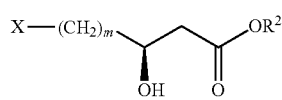

to form the compound of Formula (C):

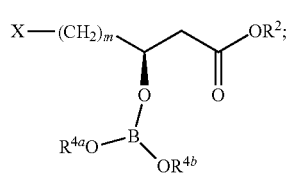

wherein:

X is a halogen;

m is an integer between 2 and 6;

$R^2$ is selected from the group consisting of, an optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl, and optionally substituted heteroaryl;

$R^{4a}$ and $R^{4b}$ are independently selected from the group consisting of an optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl, and optionally substituted heteroaryl, or $R^{4a}$ and $R^{4b}$ together with intervening atoms optionally form a 5-8 membered boron ester ring; and $R^{4c}$ is selected from the group consisting of an optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl, and optionally substituted heteroaryl.

8. The method of claim 7, wherein X is Cl; m is 2; and $R^2$, $R^{4a}$, and $R^{4b}$ are each independently a butyl group.

9. A method of making a compound of Formula (D), comprising:

reacting magnesium with a compound of Formula (C):

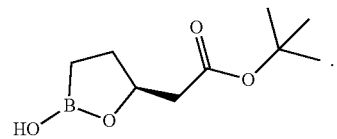

(C)

to form a first reaction intermediate; and hydrolyzing the first reaction intermediate to form the compound of Formula (D):

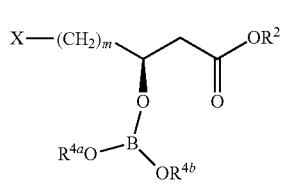

(D)

wherein:

X is a halogen;

m is an integer between 2 and 6;

$R^2$ is selected from the group consisting of, an optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl, and optionally substituted heteroaryl; and each of $R^{4a}$ and $R^{4b}$ is independently selected from the group consisting of an optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl, and optionally substituted heteroaryl, or $R^{4a}$ and $R^{4b}$ together with intervening atoms optionally form a 5-8 membered boron ester ring.

10. The method of claim 9, wherein X is Cl; m is 2; and $R^2$, $R^{4a}$, and $R^{4b}$ are independently a butyl group.

11. The method of claim 9, wherein the compound of Formula (D)

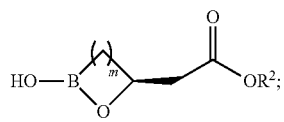

12. A method of making a compound of Formula (E), comprising reducing the ketone group of a keto-ester compound of Formula (A-1):

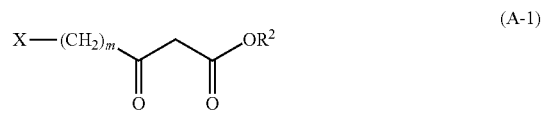

(A-1)

to form a compound of Formula (B-1):

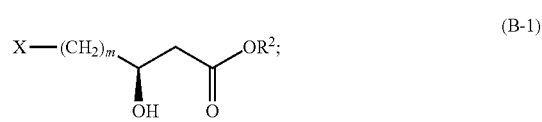

(B-1)

reacting a boronate compound $B(OR^{4a})(OR^{4b})(OR^{4c})$ with the compound of Formula (B-1) to form a compound of Formula (C):

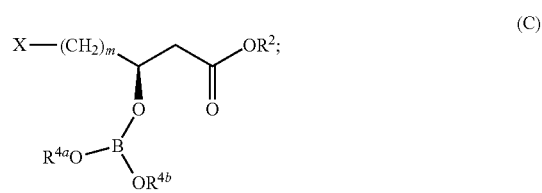

(C)

reacting magnesium with the compound of Formula (C) to form a first reaction intermediate;

hydrolyzing the first reaction intermediate to form a compound of Formula (D):

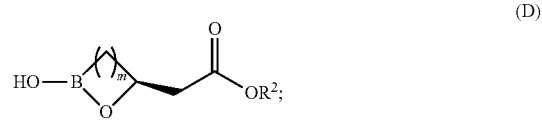

(D)

and reacting the compound of Formula (D) with a complexing agent of Formula (CL):

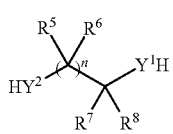

(CL)

to form the compound of Formula (E):

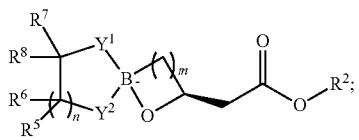

(E)

wherein:

X is a halogen;

m is an integer between 2 and 6;

n is an integer between 0 and 6;

$Y^1$ is O or $N^+R^9R^{10}$;

$Y^2$ is O or $NR^{11}$;

$R^2$ is selected from the group consisting of, an optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl, and optionally substituted heteroaryl;

$R^{4a}$ and $R^{4b}$ are independently selected from the group consisting of an optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl, and optionally substituted heteroaryl, or $R^{4a}$ and $R^{4b}$ together with intervening atoms optionally form a 5-8 membered boron ester ring;

$R^{4c}$ is selected from the group consisting of an optionally substituted $C_1$-$C_{12}$ alkyl, optionally substituted $C_3$-$C_8$ cycloalkyl, optionally substituted $C_2$-$C_{12}$ alkenyl, optionally substituted $C_2$-$C_{12}$ alkynyl, optionally substituted aryl, and optionally substituted heteroaryl;

each $R^5$ and $R^6$ is independently selected from the group consisting of H, optionally substituted phenyl, and optionally substituted $C_{1-4}$ alkyl, or $R^5$ and $R^6$ together with the atom to which they are attached, form =O;

each $R^7$ and $R^8$ is independently selected from the group consisting of H, optionally substituted phenyl, and optionally substituted $C_{1-4}$ alkyl, or $R^5$ and $R^7$ together with the atom to which they are attached form an aryl or heteroaryl ring; or $R^7$ and $R^8$ together with the atom to which they are attached, form =O; and each $R^9$, $R^{10}$ and $R^{11}$ is independently selected from the group consisting of H, optionally substituted phenyl, and optionally substituted $C_{1-4}$ alkyl.

13. The method of claim 12, wherein X is Cl, m is 2, and $R^2$ is a butyl group.

14. The method of claim 12, wherein the complexing agent of Formula (CL) is $NH_2(CH_2)_2OH$.

15. The method of claim 12, further comprising reacting the compound of Formula (E) with pinanediol to form a compound of Formula (F):

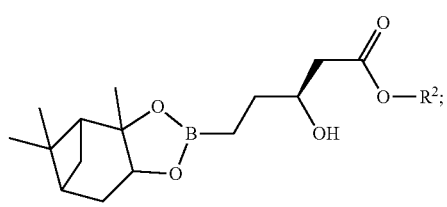

(F)

protecting the hydroxy group of the compound of Formula (F) with a PG group to form a compound of Formula (G):

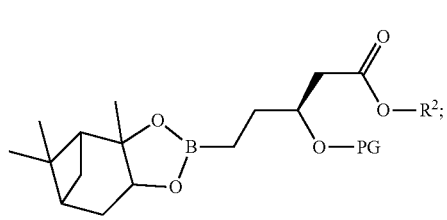

(G)

reacting the compound of Formula (G) with n-butyl-lithium and dichloromethane to form a compound of Formula (H):

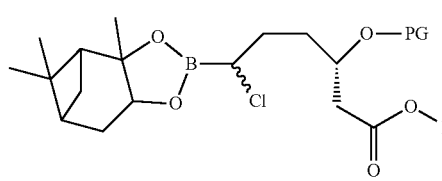

(H)

reacting the compound of Formula (H) with an LiN[Si($R^{12}$)$_3$]$_2$ to form a compound of Formula (J):

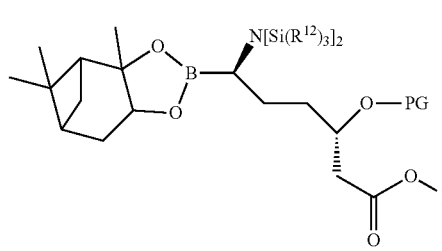

(J)

reacting the compound of Formula (J) with $R^{13}$—COCl to form a compound of Formula (K):

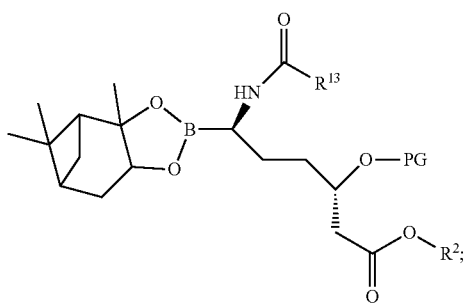
(K)

and removing the PG group on the compound of Formula (K) to form a compound of Formula (L):

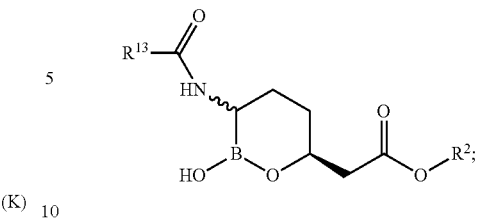
(L)

wherein:
PG is a hydroxy protection group;
$R^{12}$ is optionally substituted phenyl or optionally substituted $C_{1-8}$ alkyl; and
$R^{13}$ is selected from the group consisting of optionally substituted $C_{1-8}$ alkyl, optionally substituted $C_{0-4}$ alkyl-$C_{6-10}$ aryl, optionally substituted $C_{0-4}$ alkyl-5-10 membered heteroaryl, optionally substituted $C_{0-4}$ alkyl-$C_{3-10}$ carbocyclyl, and $C_{0-4}$ alkyl-4-10 membered heterocyclyl.

16. The method of claim 15, wherein $R^{13}$ is

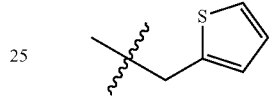

* * * * *